US012637481B2

(12) United States Patent
Reddy et al.

(10) Patent No.: US 12,637,481 B2
(45) Date of Patent: May 26, 2026

(54) BORONIC ACID DERIVATIVES AND THERAPEUTIC USES THEREOF

(71) Applicant: QPEX BIOPHARMA, INC., San Diego, CA (US)

(72) Inventors: Raja K. Reddy, San Diego, CA (US); David C. Griffith, San Marcos, CA (US); Emily Rigsbee, West Lafayette, IN (US); Serge Henri Boyer, San Diego, CA (US); Scott J. Hecker, Del Mar, CA (US); Matthew Jonathan Jones, Linz (AT)

(73) Assignee: QPEX BIOPHARMA, INC., San Diego, CA (US)

( * ) Notice: Subject to any disclaimer, the term of this patent is extended or adjusted under 35 U.S.C. 154(b) by 765 days.

(21) Appl. No.: 17/906,340

(22) PCT Filed: Mar. 17, 2021

(86) PCT No.: PCT/US2021/022799
§ 371 (c)(1),
(2) Date: Sep. 14, 2022

(87) PCT Pub. No.: WO2021/188700
PCT Pub. Date: Sep. 23, 2021

(65) Prior Publication Data
US 2023/0151029 A1     May 18, 2023

Related U.S. Application Data

(60) Provisional application No. 62/991,496, filed on Mar. 18, 2020.

(51) Int. Cl.
| | |
|---|---|
| *C07F 5/02* | (2006.01) |
| *A61K 31/69* | (2006.01) |
| *A61K 45/06* | (2006.01) |
| *A61P 31/04* | (2006.01) |

(52) U.S. Cl.
CPC .............. *C07F 5/025* (2013.01); *A61K 31/69* (2013.01); *A61K 45/06* (2013.01); *A61P 31/04* (2018.01); *C07B 2200/13* (2013.01)

(58) Field of Classification Search
CPC ..... C07F 5/025; C07B 2200/13; A61K 31/69; A61P 31/04
See application file for complete search history.

(56) References Cited

U.S. PATENT DOCUMENTS

| | | | |
|---|---|---|---|
| 3,686,398 | A | 8/1972 | Kohn et al. |
| 4,194,047 | A | 3/1980 | Christensen et al. |
| 4,260,543 | A | 4/1981 | Miller |
| 4,353,807 | A | 10/1982 | Braid |
| 4,409,214 | A | 10/1983 | Takaya et al. |
| 4,812,561 | A | 3/1989 | Hamashima et al. |
| 4,822,786 | A | 4/1989 | Zama et al. |

| | | | |
|---|---|---|---|
| 4,933,443 | A | 6/1990 | Hamashima et al. |
| 5,442,100 | A | 8/1995 | Bjorkquiest et al. |
| 5,888,998 | A | 3/1999 | Maiti et al. |
| 6,184,363 | B1 | 2/2001 | Shoichet et al. |
| 6,586,615 | B1 | 7/2003 | Kettner et al. |
| 7,271,186 | B1 | 9/2007 | Shoichet et al. |
| 7,439,253 | B2 | 10/2008 | Lampilas et al. |
| 7,582,621 | B2 | 9/2009 | Baker et al. |
| 7,612,087 | B2 | 11/2009 | Aszodi et al. |
| 7,674,913 | B2 | 3/2010 | Campbell et al. |
| 7,825,139 | B2 | 11/2010 | Campbell et al. |
| 8,680,136 | B2 | 3/2014 | Hirst et al. |
| 9,012,491 | B2 | 4/2015 | Reddy et al. |
| 9,101,638 | B2 | 8/2015 | Reddy et al. |
| 9,132,140 | B2 | 9/2015 | Reddy et al. |
| 9,156,858 | B2 | 10/2015 | Reddy et al. |
| 9,241,947 | B2 | 1/2016 | Reddy et al. |
| 9,296,763 | B2 | 3/2016 | Hirst et al. |
| 9,511,142 | B2 | 12/2016 | Burns et al. |
| 9,642,869 | B2 | 5/2017 | Reddy et al. |
| 9,687,497 | B1 | 6/2017 | Bis et al. |
| 9,694,025 | B2 | 7/2017 | Hirst et al. |
| 10,004,758 | B2 | 6/2018 | Hirst et al. |
| 10,085,999 | B1 | 10/2018 | Gordon et al. |
| 10,206,937 | B2 | 2/2019 | Reddy et al. |
| 10,294,249 | B2 | 5/2019 | Hecker et al. |
| 10,570,159 | B2 | 2/2020 | Hecker et al. |

(Continued)

FOREIGN PATENT DOCUMENTS

| | | |
|---|---|---|
| CN | 102320960 A | 1/2012 |
| CN | 106397454 A | 2/2017 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

(Continued)

*Primary Examiner* — Alicia L Otton
(74) *Attorney, Agent, or Firm* — Knobbe, Martens, Olson & Bear, LLP

(57) ABSTRACT

Disclosed herein are antimicrobial compounds, polymorphic forms, compositions, pharmaceutical compositions, the method of use and preparation thereof. Some embodiments relate to boronic acid derivatives and their use as therapeutic agents, for example, β-lactamase inhibitors (BLIs). The boronic acid derivatives disclosed herein can be used in combination with various antibiotics to treat resistant bacteria.

30 Claims, 14 Drawing Sheets

(56)                    References Cited

U.S. PATENT DOCUMENTS

| | | | |
|---|---|---|---|
| 10,618,918 B2 | 4/2020 | Hecker et al. |
| 10,662,205 B2 | 5/2020 | Hecker et al. |
| 11,180,512 B2 | 11/2021 | Hecker et al. |
| 11,286,270 B2 | 3/2022 | Hecker et al. |
| 11,999,759 B2 | 6/2024 | Hecker et al. |
| 12,016,868 B2 | 6/2024 | Reddy et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2005/0070719 A1 | 3/2005 | Belyakov et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |
| 2019/0202832 A1 | 7/2019 | Basarab et al. |
| 2021/0361682 A1 | 11/2021 | Reddy et al. |
| 2022/0056055 A1 | 2/2022 | Hecker et al. |
| 2023/0144152 A1 | 5/2023 | Lamovskaya et al. |
| 2024/0197750 A1 | 6/2024 | Griffith et al. |
| 2024/0307422 A1 | 9/2024 | Reddy et al. |
| 2024/0327426 A1 | 10/2024 | Hecker et al. |
| 2025/0002508 A1 | 1/2025 | Hecker et al. |
| 2025/0034175 A1 | 1/2025 | Hecker et al. |

FOREIGN PATENT DOCUMENTS

| | | | |
|---|---|---|---|
| CN | 106397455 A | 2/2017 |
| CN | 106397457 A | 2/2017 |
| CN | 106420617 A | 2/2017 |
| CN | 106420760 A | 2/2017 |
| CN | 106432270 A | 2/2017 |
| CN | 106432271 A | 2/2017 |
| CN | 106432272 A | 2/2017 |
| CN | 109293678 A | 2/2019 |
| EP | 1550657 A1 | 7/2005 |
| EP | 2508506 A1 | 10/2012 |
| EP | 2406233 B1 | 11/2013 |
| FR | 2573070 A1 | 5/1986 |
| JP | 2003-229277 | 8/2003 |
| JP | 2004-291253 | 10/2004 |
| WO | WO 1987/005297 A1 | 9/1987 |
| WO | WO 1989/10961 A1 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 A1 | 5/2001 |
| WO | WO 2002/022137 A1 | 3/2002 |

| | | | |
|---|---|---|---|
| WO | WO 2002/083884 A1 | 10/2002 |
| WO | WO 2003/070714 A1 | 8/2003 |
| WO | WO 2004/039859 A1 | 5/2004 |
| WO | WO 2004/058679 A2 | 7/2004 |
| WO | WO 2004/064755 A2 | 8/2004 |
| WO | WO 2005/033090 A1 | 4/2005 |
| WO | WO 2005/035532 A1 | 4/2005 |
| WO | WO 2005/087700 A2 | 9/2005 |
| WO | WO 2006/052733 A1 | 5/2006 |
| WO | WO 2006/091771 A2 | 8/2006 |
| WO | WO 2007/058602 A2 | 5/2007 |
| WO | WO 2007/065288 A2 | 6/2007 |
| WO | WO 2007/095638 A2 | 8/2007 |
| WO | WO 2008/039420 A2 | 4/2008 |
| WO | WO 2008/116813 A2 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |
| WO | WO 2016/116892 A1 | 7/2016 |
| WO | WO 2016/149393 A1 | 9/2016 |
| WO | WO 2017/100537 A1 | 6/2017 |
| WO | WO 2018/005662 A1 | 1/2018 |
| WO | WO 2018/013870 A1 | 1/2018 |
| WO | WO 2019/075084 A1 | 4/2019 |
| WO | WO 2019/093450 A1 | 5/2019 |
| WO | WO 2020/112542 A1 | 6/2020 |
| WO | WO 2021/041616 A1 | 3/2021 |
| WO | WO 2021/188700 A1 | 9/2021 |

OTHER PUBLICATIONS

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

(56) References Cited

OTHER PUBLICATIONS

Arya et al., "Advances in asymmetric enolate methodology", Tetrahedron (2000) 56:917-947.
Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.
Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Berkhout et al., "Pharmacodynamics of Ceftazidime and Avibactam in Neutropenic Mice with Thigh or Lung Infection", Antimicrob Agents Chemother. (2015) 60 (1): 368-375.
Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.
Biedrzycki et al., "Derivatives of tetrahedral boronic acids", J. Organomet. Chem. (1992) 431:255-270.
Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.
Bowker et al., Comparative pharmacodynamics of meropenem using an in-vitro model to simulate once, twice and three times daily dosing in humans. J Antimicrob Chemother (1998) 42: 461-467.
Brabez et al., "Design, synthesis, and biological studies of efficient multivalent melanotropin ligands: tools toward melanoma diagnosis and treatment", J Med Chem. (2011) 54(20):7375-7384.
Braisted et al., "Discovery of a potent small molecule IL-2 inhibitor through fragment assembly", J Am Chem Soc., (2003) 125(13): 3714-3715; Supporting Information, 42 pages.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (2014/03) 79(8): 3671-3677.
Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.
Bundgaard H. [Ed.], "Design of Prodrugs", Elsevier (1985); TOC, 2 pages.
Bush et al., "Minireview: Updated Functional Classification of beta-Lactamases," Antimicrob Agents Chemo. (2010) 54(3):969-976.
CAS Registry No. 2005:329437 CAPLUS; "Product subclass 28: Vinylboranes", Vaultier et al., (2004); XP-002764965; 1 page.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
CAS Registry No. 831209-98-4 6H-Dibenz[c,e][1,2]oxaborin, 6a, 10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
CAS Registry No. 2114651-20-4; "7-Benzofurancarboxylic acid", Aurora Fine Chemicals; Aug. 16, 2017; 1 page.

CAS Registry No. 1780853-40-8; "7-Benzofurancarboxylic acid", Aurora Fine Chemicals; Jun. 15, 2015; 1 page.
CAS Registry No. 1427326-65-5; "7-Benzofurancarboxylic acid", Ellanova Laboratories; Apr. 5, 2013; 1 page.
CAS Registry No. 1344904-36-4; "7-Benzofurancarboxylic acid", Asiba Pharmatech, Inc.; Nov. 13, 2011; 1 page.
CAS Registry No. 1890373-92-8; "Benzoic acid", Aurora Fine Chemicals; Apr. 15, 2016; 1 page.
CAS Accession Number 2006320-60-9; "3,4-dihydro-2-hydroxy-2H-1,2-Oxaborino[6,5-c]pyridine-8-carboxylic acid", CAS, (Oct. 5, 2016), Database accession No. 2006320-60-9, URL: STN.
CAS Registry No. 2170834-63-4; 'Benzo[e]cycloprop[c][1,2]oxaborin-4-carboxylic acid, 5-fluoro-1,1a,2,7b-tetrahydro-2-hydroxy-, (1aR,7bS); Jan. 23, 2018; 1 Page.
CAS Registry No. 2170848-99-2; 'Borate(2), [3-[(1 S2R)-cyclopropyl-Kc2]-6-fluoro-2-(hydroxy-кO)benzoato(3-)]dihydroxy-, sodium (1:2), (t-4)'; Jan. 24, 2018; ? Page.-carboxylic acid, 5-fluoro-1, 1a,2,7b-tetrahydro-2-hydroxy-, (1aR,7bS)'; Jan. 23, 2018; 1 Page.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from <//www.chemicalland21.com/lifescience/phar/N-METHYL-D-GLUCAMINE.htm>; 2 pages.
Chinchilla et al., "Recent advances in Sonogashira reactions", Chem Soc Rev., (2011) 40: 5084-5121.
Clark et al., "Concise synthesis of the C-1-C-12 fragment of amphidinolides T1-T5", Org Biomol Chem. (2011) 9(13): 4823-4830.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Cornella et al., "Ni-catalyzed stereoselective arylation of inert C—O bonds at low temperatures". Org Lett. (2013) 15(24):6298-6301 with Supporting Information in 50 pages.
Coutts et al., "Two Efficient Methods For The Cleavage of Pinanediol Boronate Esters Yielding The Free Boronic Acids", Tetrahedron Lett. (1994) 35(29):5109-5112.

(56)         References Cited

OTHER PUBLICATIONS

Craig Wa., "Pharmacokinetic/pharmacodynamic parameters: rationale for antibacterial dosing of mice and men", Clin Infect Dis. (1998) 26(1): 1-10.

Cunha, "Meropenem in elderly and renally impaired patients", Int'l J Antimicro Agents (1998) 10: 107-117.

Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.

Darses et al., "Potassium Organotrifluoroborates: New Perspectives in organic Synthesis", Chem Rev. (2008) 108:288-325.

Davoli et al., "Enantioselective total synthesis of (-)-microcarpalide", Tetrahedron (2005) 61:4427-4436.

De Meijere A. [Ed], Science of Synthesis—vol. 24; "Three Carbon-Heteroatom Bonds: Ketene Acetals and Yne-X Compounds", TOC 46 pages.

Di Gioia et al., "Optically Pure N-Hydroxy-O-triisopropylsilyl-alpha-L-amino Acid Methyl Esters from AICI3-Assisted Ring Opening of Chiral Oxaziridines by Nitrogen Containing Nucleophiles", J Org Chem. (2005) 70(25):10494-10501.

Dörwald F.Z., Side Reactions in Organic Synthesis—A guide to Successful Synthesis Design, Wiley-VCH Verlag Gmbh & Co. KGaA, Weinheim, Germany (2005); Preface in 4 pages.

Drawz et al., "Three Decades of beta-Lactamase Inhibitors", Clin Microbiol Reviews (Jan. 2010) 23(1):160-201.

Drusano et al., Meropenem: clinical response in relation to in vitro susceptibility. Clin Microbiol Infect. (2000) 6: 185-194.

Dunetz et al., "Large-scale applications of amide coupling reagents for the synthesis of pharmaceuticals", Org Process Res Develop. (2016) 20(2): 140-177.

Eggen et al., "Total synthesis of cryptophycin-24 (Arenastatin A) amenable to structural modifications in the C16 side chain", J Org Chem. (2000) 65(23): 7792-7799; and Supporting documents, 22 pages.

Eidam et al., "Design, synthesis, crystal structures and antimicrobial activity of sulfonamide boronic acids as beta-lactamase inhibitors", J Med Chem. (2010) 53(21):7852-7863.

Eissenstat et al., "Aminoalkylindoles: Structure-Activity Relationships of Novel Cannabinoid Mimetics", J Med Chem. (1995) 38(16):3094-3105.

El Nezhawy et al., "Synthesis and antioxidant activity of some thiazolidin-4-one derivatives", Springer; Chemical Monthly/Monatshefte für Chemie (2009) 140(5):531-539.

Endo et al., "Chemoselective Suzuki coupling of diborylmethane for facile synthesis of benzylboronates", Org Lett. (2011) 13(13):3368-3371.

Fan, et al. (2009): STN International HCAPLUS database, Columbus (OH), accession No. 2009: 425839; 6 pages.

Farquhar et al., "Intensely potent doxorubicin analogues: structure-activity relationship", J. Med. Chem. (1998) 41(6):965-972.

Ghosh et al., "Enantioselective total synthesis of (+)-largazole, a potent inhibitor of histone deacetylase", Org Lett. (2008) 10(17):3907-3909.

Giroux, A., "Synthesis of benzylic boronates via palladium-catalyzed cross-coupling reaction of bis(pinacolato)diboron with benzylic halides", Tetrahedron Lett. (2003) 44:233-235.

Gorovoy et al., "Boron-Containing Peptidomimetics—A Novel Class of Selective Anti-tubercular Drugs", Chem Biol Drug Des. (Jan. 2013) 81(3):408-413.

Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.

Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.

Greene, et al., "Greene's Protective Groups in Organic Synthesis", 4th Edition, (2007); pp. 774, 785 & 787.

Gunanathan et al., "Ruthenium catalyzed hydroboration of terminal alkynes to Z vinylboronates", J Am Chem Soc. (2012) 134(35): 14349-14352; Supporting Information, 32 pages.

Hall D.G., [Ed], Boronic Acids [vol. 2]: Preparations and applications in Organic Synthesis, Medicine and Materials, Wiley-VCH, Weinheim, 2nd Edition (2011); TOC.

Hama et al., "Palladium-Catalyzed alpha-Arylation of Zinc Enolates of Esters: Reaction Conditions and Substrate Scope", J Org Chem. (2013) 78(17): 8250-8266.

Hartung et al., "Highly Z-selective and Enantioselective Ring Opening/Cross Metathesis Catalyzed by Resolved Stereogenic-At-Ru Complex", J Am Chem Soc. (2013/07) 135(28): 10183-10185.

He et al., "Ligand-promoted borylation of C(sp3)—H bonds with palladium(II) catalysts", Angew Chem Int Ed., (2016) 55(2): 785-789.

Hecker et al., "Discovery of a Cyclic Boronic Acid beta-Lactamase Inhibitor (RPX7009) with Utility vs Class A Serine Carbapenemases", J Med Chem. (2015/03) 58:3682-3692.

Higuchi et al., [Eds.] "Pro-drugs as Novel Drug Delivery Systems", ACS Sumposium Series 14 (1975); TOC, 3 pages.

Hong et al., "Ceftolozane/tazobactam: A Novel Antipseudomonal Cephalosporin and β-lactamase-inhibitor Combination", Infect Drug Resist. (2013) 6: 215-223.

Höpfl et al., "Dynamic NMR and X-ray diffraction study of (N—B)-diphenyl(2-aminoethoxy) borane derivatives of ephedrines and pseudoephedrines". J Organomet Chem. (1997) 544(2):175-188.

Hoveyda A., "Evolution of catalytic stereoselective olefin metathesis: From ancillary transformation to purveyor of stereochemical identity", J Org Chem. (2014/06) 79(11): 4763-4792.

Hu et al., "Ag(I)-catalyzed C—H borylation of terminal alkynes", Tetrahedron (2014) 70: 5815-5819.

Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.

Inglis et al., "Observations on the Deprotection of Pinanediol and Pinacol Boronate Esters via Fluorinated Intermediates", J Org Chem. (2010) 75(2):468-471; Supporting Information, S 1-S-76.

Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.

Ito et al., "An efficient constructive method for a tricyclic system: an important intermediate for the synthesis of tricycloclavulone", Tetrahedron Lett. (2003) 44:1259-1261.

Jadhav et al., "Direct synthesis of [alpha-[(tert-Butoxycarbonyl)amino]alkyl]-boronates from (alpha-Haloalkyl)boronates", Org Chem. (1996) 61(22):7951-7954.

Jagannathan et al., "Synthesis of Boronic Acid Analogues of alpha-Amino Acids by Introducing Side Chains as Electrophiles", J Org Chem. (2001) 66(19):6375-6380.

Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.

Jarrett et al., "Nickel(II) bis(phosphine) complexes". Inorg Chem. (1991) 30(9):2098-2104 with Supporting Information in 7 pages.

Jiang et al., "A Practical Synthesis of Cefcapene Pivoxil", Synthesis (2012) 44:207-214.

Johnson et al., "A drug targeting motif for glycosidase inhibitors: An iminosugar-boronate shows unexpectedly selective beta-galactosidase inhibition", Tetrahed Lttrs. (2002) 43(49):8905-8908.

Jordan V.C., "Tamoxifen: A most unlikely pioneering medicine", Drug Discovery (2003) 2:205-213.

Kabalka et al., "Synthesis of a series of bornonated unnatural cyclic amino acids as potential boron neutron capture therapy agents", Appl Organomet Chem. (2008) 22(9):516-522.

Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.

(56) References Cited

OTHER PUBLICATIONS

Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.

Kikuchi et al., "Comparison of the Pharmacodynamics of Biapenem in Bronchial Epithelial Lining Fluidin Healthy Volunteers Given Half-Hour and Three-Hour Intravenous Infusions", Antimicrob Agents Chemother. (2009/07) 53(7):2799-2803.

Kint et al., "New-found fundamentals of bacterial persistence", Trends Microbiol. (2012) 20(12):577-585.

Kinuta et al., "Rhodium-catalyzed borylation of aryl 2-pyridyl ethers through cleavage of the carbon-oxygen bond: borylative removal of the directing group". J Am Chem Soc. (2015) 137(4):1593-1600 with Supporting Information in 198 pages.

Kondo et al., Ruthenium-Catalyzed Monoalkenylation of Aromatic Ketones by Cleavage of Carbon-Heteroatom Bonds with Unconventional Chemoselectivity. Angew Chem Int Ed Engl. (2015) 54(32):9293-9297 with Supporting Information in 95 pages.

Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.

Kotha et al., "Recent applications of the suzuki-miyaura cross-coupling reaction in organic synthesis", Tetrahedron (2002) 58:9633-9695.

Kuang et al., "Convenient and stereoselctive synthesis of (Z)-1-bromo-1-alkenes by microwave-induced reaction", Tetrahedron Letts. (2001) 42(23): 3893-3896.

Kumar et al., "Synthesis of intermediates for the lactone moiety of mevinic acids via tellurium chemistry", J. Org. Chem., (1994) 59(17):4760-4764.

Kumar et al., "Development of Practical Methodologies for the Synthesis of Functionalized Benzoboroxoles", Tetrahedron Lett. (2010/08/25) 51(34):4482-4485.

Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.

Kuti et al., "Use of Monte Carlo simulation to design an optimized pharmacodynamic dosing strategy for meropenem", J Clin Pharmacol. (2003/10) 43(10): 1116-1123 with Erratum (2005); 1 page.

Laitar et al., "Catalytic diboration of aldehydes via insertion into the copper-boron bond", J Am Chem Soc. (2006) 128(34):11036-11037.

Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.

Larock R. [Ed.] Comprehensive Organic Transformations, VCH Publishers 1989; TOC, 11 pages.

Lebel et al., "Boc-protected amines via a mild and efficient one-pot Curtius rearrangement", Org Letts. (2005) 7(19): 4107-4110.

Lee et al., "Vicinal Diboronates in High Enantiomeric Purity through Tandem Site-Selective NHC—Cu-Catalyzed Boron-Copper Additions to Terminal Alkynes", J Am Chem Soc. (Dec. 2009) 131(51):18234-18235.

Lee et al., "Comparison of 30-min and 3-h infusion regimens for imipenem/cilastatin and for meropenem evaluated by Monte Carlo simulation", Diagn Microbiol Infect Dis. (2010) 68: 251-258.

Li et al., "Population Pharmacokinetic Analysis and Dosing Regimen Optimization of Meropenem in Adult Patients", J Clin Pharmacol. (2006) 46(10): 1171-1178.

Li et al, "Novel macrocyclic Hcv NS3 protease inhibitors derived from a-amino cyclic boronates", Bioorganic Med Chem Lett. (2010) 20:5695-5700.

Li et al., "Synthesis and evaluation of novel alpha-amino cyclic boronates as inhibitors of Hcv NS3 protease", Bioorg Med Chem Lett. (2010) 20:3550-3556.

Li et al., "Stereoselective total synthesis of etnangien and etnangien methyl ester", J Org Chem. (2010) 75(8):2429-2444.

Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.

Lima et al., "Bioisosterism: A Useful Strategy for Molecular Modification and Drug Design", Curr Med Chem. (2005) 12:23-49.

Lin et al., "Pharmacokinetics and dose proportionality of ceftibuten in men", Antimicro Agents Chemother. (1995) 39(2): 359-361.

Lin et al., "Enantioselective syn and anti homocrotylation of aldehydes: Application to the formal synthesis of spongidepsin", J Am Chem Soc. (2015) 137(40): 13176-13182; Supporting Information, 177 pages.

Liu et al., "Selective Protein tyrosine phosphatase 1B inhibitors: Targeting the second phosphotyrosinebinding site with non-carboxylic acid-containing ligands", J Med Chem. (2003) 46(16):3437-3440; Supporting Information, 38 pages.

Liu et al., "Application of Stereoselective Ether Transfer to the Synthesis of Isotactic Polyethers", J Org Chem. (2010) 75(12):3953-3957.

Livermore et al., "Activities of NXL104 combinations with Ceftazidime and Aztreonam against Carbapenemase-producing Enterobacteriaceae", Antimicr Agents Chemother. (2011) 55(1):390-394.

Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.

Lodise et al., "Penetration of meropenem into epithelial lining fluid of patients with ventilator-associated pneumonia", Antimicrob Agents Chemother. (Apr. 2011) 55(4):1606-1610.

Louie et al., Impact of meropenem in combination with tobramycin in a murine model of Pseudomonas aeruginosa pneumonia. Antimicrob Agents Chemother (2013) 57: 2788-2792.

Luithle et al., "Synthesis of enantiomerically pure cis-cyclopropylboronic esters", Eur J Org Chem. (2000) 14: 2557-2562.

MacVane et al., Characterizing in vivo pharmacodynamics of carbapenems against Acinetobacter baumannii in a Murine thigh infection model to support breakpoint determinations. Antimicrob Agents Chemother (2014) 58: 599-601.

Maguire B. A., Inhibition of Bacterial Ribosome Assembly: a Suitable Drug Target? Microbiol Mol Biol Rev. (2009) 73(1):22-35.

Malfertheiner et al., "Current concepts in the management of Helicobacter pylori infection: the Maastricht III Consensus Report", Gut (2007) 56(6):772-781.

Matteson et al., "Iodomethaneboronic Esters and Aminomethaneboronic Esters", J Organomet. Chem. (1979) 170:259-264.

Matteson et al., "A Directed Chiral Synthesis of Amino Acids from Boronic Esters", Tetrahedron Lett. (1987) 28(39):4499-4502.

Matteson, D.S., "Asymmetric Synthesis with Boronic Esters", Acc Chem Res. (1988) 21(8):294-300.

Matteson, "Boronic esters in stereodirected synthesis", Tetrahedron (1989) 45(7):1859-1885.

Matteson et al., "A stereospecific convergent coupling of nucleophilic and electrophilic chiral carbons", J. Am. Chem. Soc. (1989) 111:4399-4402.

Matteson et al., "Synthesis of asymmetrically deuterated glycerol and dibenzylglyceraldehyde via boronic esters", J. Am. Chem. Soc. (1990) 112:3964-3969.

Matteson et al., "(Alkoxyalkyl)boronic Ester Intermediates for Asymmetric Synthesis", Organometallics (1996) 15:152-163.

Matteson, "Alpha-Halo Baronic Esters in Asymmetric Synthesis", Tetrahedron (1998) 54(36):10555-10607.

Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).

Matteson et al., "Cesium Alkyltrifluoroborates from Asymmetric Boronic Esters", Synlett (Jul. 2006) 20:3501-3503.

Matteson et al., "Synthesis of a (Beta-acetamido-alpha-acetoxyethyl) boronic ester via azido boronic esters", J Organomet Chem. (2008) 693:2258-2262.

Matteson, "Boronic Esters in Asymmetric Synthesis", J Org Chem. (Oct. 2013) 78(20): 10009-10023.

(56) References Cited

OTHER PUBLICATIONS

McOmie J.R.W. [Ed], Protective Groups in Organic Chemistry, Plenum Press, London & New York (1973); TOC, 3 pages.
Meanwell, "Synopsis of some recent tactical application of bioisosteres in drug design", J. Med. Chem. (2011) 54:2529-2591.
McSharry et al., "Prediction of the pharmacodynamically linked variable of oseltamivir carboxylate forinfluenza A virus using an in vitro hollow-fiber infection model system", Antimicrob Agents Chemother (2009) 53(6): 2375-2381.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Miriagou et al., "Acquired carbapenemases in Gram-negative bacterial pathogens: detection and surveillance issues", Clin Microbiol Infect. (Feb. 2010) 16(2):112-122.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Monogue et al., "Efficacy of Humanized Exposures of Cefiderocol (S-649266) against a DiversePopulation of Gram-negative Bacteria in a Murine Thigh Infection Model", Antimicrob Agents Chemother. (2017) 61(11): e01022-17 in 10 pages.
Morandi et al., "Structure-based optimization of cephalothin-analogue boronic acids as beta- lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81: 1-13.
Morrill et al., "Treatment Options for Carbapenem-Resistant Enterobacteriaceae Infections", Open Forum Infectious Diseases [OFID] Apr. 2015; 15 pages.
Munar et al., "Drug Dosing Adjustments in Patients with Chronic Kidney Disease", Am Fam Physician (May 2007) 75(1): 1487-1496.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillinin an In Vitro Infection Model", Antimicrob Agents Chemother. (2016) 60: 2075-2080. doi: 10.1128/AAC.02747-15.
Nicolau DP., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How to Detect NDM-1 Producers, J. Clin. Micro. (2011) 49:718-721.
O'Brien et al., "Enantioselective Synthesis of Boron-Substituted Quaternary Carbons by NHC—Cu-Catalyzed Boronate Conjugate Additions to Unsaturated Carboxylic Esters, Ketones or Thioesters." J Am Chem Soc. (2010) 132(31): 10630-10633.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta. gamma.-unsaturated esters. Documentation of an alkoxy-directed hydroboration reaction", J. Org. Chem. (1992) 57(20):5288-5290.
Paquette L.A. [Ed.] Encyclopedia of Reagents for Organic Synthesis, vol. 1; J. Wiley & Sons (1995); Cover Only.
Patani et al., "Bioisosterism: A Rational Approach in Drug Design", Chem Rev. (1996) 96:3147-3176.

Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Pietruszka et al., "Enantiomerically pure cyclopropylamines from cyclopropylboronic esters", Eur J Org Chem. (2009) 34: 5998-6008.
Pine et al., "Resonance vs. Tautomerism" in Organic Chemistry; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Queenan et al., "Carbapenemases: the Versatile β-Lactamases", Clin Microbiol Rev. (Jun. 2007) 20(3): 440-458.
Rehm et al., "Staphylococcus aureus: Methicillin-susceptible S. aureus to Methicillin-resistant S. aureus and Vancomycin-resistant S. aureus", Clin Inf Diseases. (2010) 51(S2):S176-S182.
Reich et al., "Organoselenium chemistry. Alkylation of acid, ester, amide, and ketone enolates with bromomethyl benzyl selenide and sulfide. Preparation of selenocysteine derivatives", J Organ Chem. (1986) 51(15): 2981-2988.
Reissig et al., "High diastereoselection in the alkylation of siloxy-substituted methyl cyclopropanecarboxylates: consequence of a pyramidal ester enolate anion?", J. Am. Chem. Soc. (1982) 104:1735-1737.
Rhoads et al., "The Claisen and Cope Rearrangements", Organic Reactions Chapter 1 (1975) 22: 1-66.
Robak et al., "Synthesis and applications of tert-butanesulfinamide", Chem Rev. (2010) 110(6):3600-3740.
Roche, E.B. (Ed.)., Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from Escherichia coli and Klebsiella pneumoniae", Antimicro Agents Chemother. (2010) 54(1):471-476.
Rosen et al., "Nickel-catalyzed cross-couplings involving carbon-oxygen bonds". Chem Rev. (2011) 111(3):1346-1416.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sabet et al., "Activity of Simulated Human Dosage Regimens of Meropenem and Vaborbactamlagainst Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.
Saito et al., "Nickel-catalyzed boron insertion into the C2—O bond of benzofurans". J Am Chem Soc. (2016)., 138(47), 15315-15318 with Supporting Information in 103 pages.
Sawant et al., "Synthesis of the C1-C13 Fragment of Biselyngbyaside", Synlett (2011) 20: 3002-3004.
Sawyer et al., "Physical properties and synthetic utility of a-alkoxyorganolithium species as studied through ligand selectivity in tin-lithium exchange", J. Am. Chem. Soc. (1988) 110:842-853.
Schwarzer et al., "Combined theoretical and experimental studies of nickel-catalyzed cross-coupling of methoxyarenes with arylboronic esters via C—O bond cleavage". J Am Chem Soc. (2017) 139(30):10347-10358 with Suppl. Information in 255 pages.
Scriven et al., "Azides: Their preparation and synthetic uses", Chem Rev. (1988) 88(2): 297-368.
Selander et al., "Palladium-catalyzed allylic C—OH functionalization for efficient synthesis of functionalized allylsilanes", J Am Chem Soc. (2011) 133(3):409-411.

(56)         References Cited

OTHER PUBLICATIONS

Shaffer, Robyn Kroop, "The Challenge of Antibiotic-Resistant *Staphylococcus*: Lessons from Hospital Nurseries in the mid-20th Century", Yale J Biol Med. (2013) 86:261-270.

Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.

Singer et al., "Catalytic, enantioselective acetate aldol additions to alpha-, beta-ynals: Preparation of optically active propargylic alcohols", Tetrahedron (1998) 54(25): 7025-7032.

Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.

Singh et al., "Confronting the challenges of discovery of novel antibacterial agents", Bioorg Med Chem Lett. (2014) 24(16):3683-3689.

Sliwka et al., "Synthetic Sulfur Carotenoids II: Optically Active Carotenoid Thiols", Tetrahedron: Asymmetry (1993) 4(3):361-368.

Solladié et al., "First Stereocontrolled Synthesis of the (3S,5R,7R, 10R, 11R)-C1-C13 Fragment of Nystatin A(1)", J Org Chem. (1999) 64(15):5447-5452.

Souto et al., "Synthesis and biological characterization of the histone deacetylase inhibitor largazole and c7-modified analogues", J. Med. Chem. (2010) 53(12):4654-4667.

Spiegel et al., "CP-263, 114 synthetic studies. Construction of an isotwistane ring system via rhodium carbenoid C—H insertion", Tetrahedron (2002) 58:6545-6554.

Stivala et al., "Highly enantioselective direct alkylation of arylacetic acids with chiral lithium amides as traceless auxiliaries." J Am Chem Soc., (2011)133(31): 11936-11939.

Sumida et al., "Boron-selective biaryl coupling approach to versatile dibenzoxaborins and application to concise synthesis of defucogilvocarcin M", Org Ltt. (2014/12) 16(23):6240-6243.

Sun et al., "A method for the deprotection of alkylpinacolyl boronate esters", J Org Chem. (2011) 76(9): 3571-3575; Supporting Information, 8 pages.

Sun et al., "Programmed Synthesis of a Contiguous Stereotriad Motif by Triple Stereospecific Reagent- controlled Homologation", Org Lttr. (Jul. 2013) 15(17):4500-4503.

Tam et al., "Optimization of meropenem minimum concentration/ MIC ratio to suppress in vitro resistance of Pseudomonas aeruginosa", Antimicrob Agents Chemother. (2005) 49(12): 4920-4927.

Tang et al., "New Chiral Phosphorus Ligands for Enantioselective Hydrogenation." Chem Rev. (2003) 103: 3029-3070.

Teo et al., "Efficient and highly aldehyde selective Wacker oxidation", Org Lett. (2012) 14(13):3237-3239.

Theuretzbacher et al., "Update on antibacterial and antifungal drugs—can we master the resistance crisis?", Curr Opin Pharmacol. (2011) 11:429-432.

Tobisu et al., "Nickel-catalyzed alkylative cross-coupling of anisoles with Grignard reagents via C—O bond activation". J Am Chem Soc. (2016) 138(47):6711 and Suppl. Information in 105 pages.

Ty et al., "Synthesis and biological evaluation of enantiomerically pure cyclopropyl analogues of combretastatin A4". Bioorg Med Chem (2013) 21:1357-1366.

U.S. Department of Health and Human Resources, "Antibiotic Resistance Threats in the United States, 2013"; 114 pages.

Valters et al., "Ring-Chain Tautomerism", Plenum Press, New York and London, Softcover reprint of the hardcover 1st Ed. 1985, Chapter 1, 23 pages.

VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/ AAC.02513-12.

Vasil'ev et al., (1977): STN International HCAPLUS database, Columbus (OH), accession No. 1977: 72730; 1 page.

Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.

Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.

Waley, Stephen G., "A quick method for the determination of inhibition constants", Biochem J. (1982) 205(3):631-633.

Walker et al., "Pharmacodynamic activities of meropenem in an animal infection model", (1994), Abstracts of Papers #A91, 34th Interscience Conference on Antimicrobial Agents and Chemotherapy, Orlando , FL., 5 pages.

Walsh et al., "Metallo-beta-Lactamases: the Quiet before the Storm?", Clin Microbiol Rev. (2005) 18(2):306-325.

Wang et al., "Recognition and resistance in TEM beta-lactamase", Biochemistry (2003) 42(28):8434-8444.

Webb et al., "Metal catalysed hydroboration of vinyl sulfides, sulfoxides, sulfones, and sulfonates", J Mol Cat A: Chem. (2007) 275:91-100.

Wenkert et al., "Nickel-induced conversion of carbon-oxygen into carbon-carbon bonds. One-step transformations of enol ethers into olefins and aryl ethers into biaryls".(1979) 101(8):2246-2247.

Wilson D.N., "The A-Z of bacterial translation inhibitors", Crit Rev Biochem Mol Biolog. (2009) 44(6):393-433.

Wohlrab et al., "Total synthesis of plusbacin A3: a depsipeptide antibiotic active against vancomycin-resistant bacteria", J. Am. Chem. Soc. (2007) 129:4175-4177.

Wong et al., "A chemoselective Reformatsky-Negishi approach to α-haloaryl esters", Tetrahedron (2014) 70(7): 1508-1515.

Xia et al., "Synthesis and SAR of novel benzoxaboroles as a new class of beta-lactamase inhibitors", Bioorg Med Chem Lett. (2011) 21:2533-2536.

Xie et al., "Group-assisted purification (GAP) chemistry for the synthesis of Velcade via asymmetric borylation of N-phosphinylimines", Beilstein J Org Chem (Mar. 2014) 10:746-751.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005) 46(46):7899-7903.

Zhang et al., "Catalytic boracarboxylation of alkynes with diborane and carbon dioxide by an N-heterocyclic carbene copper catalyst." J Am Chem Soc. (2012) 134(35): 14314-14317.

Zhu et al., "Design, preparation, x-ray crystal structure, and reactivity of o-alkoxyphenyliodoniumbis(methoxycarbonyl)methanide, a highly soluble carbene precursor", Org Lett. (2012) 14(12): 3170-3173; Supporting Information, 76 pages.

Allen et al., "Ansel's Pharmaceutical Dosage Forms and Drug Delivery Systems", 8th Edition (2004) TOC only.

Balbach et al., "Pharmaceutical evaluation of early development candidates 'the 100 mg-approach'", Int'l J Pharma. May 4, 2004;275: 1-12.

Banker G.S. et al. [Eds.], Modern Pharmaceutics, 4th Edition; Marcel Dekker, Inc. (2002); Chapters 9 and 10, 98 pages.

Bou et al., "Cloning, nucleotide sequencing, and analysis of the gene encoding an AmpC beta-lactamase in Acinetobacter baumannii", Antimicrob Agents Chemother (2000) 44(2):428-432.

Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.

Goodman et al., [Eds.], "The Pharmacological Basis of Therapeutics", 8th. Edition, Pergamon Press (1990); TOC, 8 pages.

Hecker et al., "Discovery of Cyclic Boronic Acid QPX7728, an Ultrabroad-Spectrum Inhibitor of Serine and Metallo-β-lactamases", J Med Chem. (Mar. 2020) 63: 7491-7507.

(56) References Cited

OTHER PUBLICATIONS

Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.

Lieberman H.A. [Ed] Pharmaceutical Dosage Forms—Tablets; Marcel Dekker, Inc. (1989) 2nd Ed; TOC; 7 pages.

Montefour et al., "Acinetobacter baumannii: an emerging multidrug-resistant pathogen in critical care", Crit Care Nurse (2008) 28(1):15-25.

Nema et al., "Excipients and Their Role in Approved Injectable Products: Current Usage and Future Directions", PDA J Pharm Sci Technol. (2011) 65(3):287-332.

Perez et al., "Why are we afraid of *Acinetobacter baumannii*?", Expert Rev Anti Infect Ther. (2008) 6(3): 269-71.

Powell et al., "Compendium of excipients for parenteral formulations", PDA J Pharm Sci Technol. (1998) 52(5):238-311.

Roy et al., "Polymorph discrimination using low wavenumber Raman spectroscopy". Org Process Res Dev. Jul. 19, 2013;17(7):976-980.

Singhal et al., "Drug polymorphism and dosage form design: A practical perspective", Adv Drug Deliv Rev. Feb. 23, 2004;56(3): 335-347.

International Search Report and Written Opinion dated May 28, 2021, for International Application No. PCT/US2021/022799, filed Mar. 17, 2021.

Byrn et al., "Pharmaceutical Solids: A Strategic Approach to Regulatory Considerations". Pharma Res. Jul. 1995;12(7):945-954.

Cahill et al., Cyclic Boronates Inhibit All Classes of β-Lactamases. Antimicro Age Chemother. Apr. 2017;61(4): e02260-16.

CAS Registry No. 1964:447952 CAPLUS; "Arylboronic acids. VII. Some reactions of o-formylbenzenebornic acid", Tschampel et al. J Org Chem. Aug. 1964;29(8): 2168-2172; Abstract.

Grant, D.J.W., "Theory and Origin of Polymorphism". in Polymorphism in Pharmaceutical Solids, Harry G. Brittain [Ed], Drugs Pharma Sciences 2nd Ed., (Dec. 31, 1999), Chapter 1; pp. 1-10.

Guillory J.K., "Generation of Polymorphs, Hydrates, Solvates, and Amorphous Solids" in Polymorphism in Pharmaceutical Solids, Harry G. Brittain [Ed], Drugs Pharma Sciences 2nd Ed., (12-31-1999), Chapter 5; pp. 183-226. (3-part doc).

Gupta et al., "Salts of Therapeutic Agents: Chemical, Physiocochemical, and Biological Considerations". Molecules. Jul. 14, 2018;23(7):1719 in 15 pages.

Hosokawa, R., "Conductivity Measurement / General Tests", The Japanese Pharmacopoeia, Sixteenth Edition, Mar. 2011, pp. 64-68, 2070.

Ito et al., In vitro antimicrobial activity of S-649266, a catechol-substituted siderophore cephalosporin, when tested against non-fermenting Gram-negative bacteria. J Antimic Chemother. Mar. 1, 2016;71(3):670-677.

Lomovskaya et al., Impact of intrinsic resistance mechanisms on potency of QPX7728, a new ultrabroad-spectrum beta-lactamase inhibitor of serine and metallo-beta-lactamases in Enterobacteriaceae, Pseudomonas aeruginosa, and Acinetobacter baumannii. Antimicrobial agents and chemotherapy. May 21, 2020;64(6):e00552-20 in 11 pages.

Lomovskaya et al., Spectrum of Beta-lactamase inhibition by the cyclic boronate QPX7728, an ultrabroad-spectrum beta-lactamase inhibitor of serine and metallo-beta-lactamases: enhancement of activity of multiple antibiotics against isogenic strains expressing single beta-lactamases. Antimicrobial Agents and Chemotherapy. May 21, 2020;64(6):e00212-20 in 9 pages.

Pettersson et al., Discovery of cyclopropyl chromane-derived pyridopyrazine-1, 6-dione γ-secretase modulators with robust central efficacy. MedChemComm. 2017;8(4): 730-743.

Serajuddin A.T.M., "Salt formation to improve drug solubility". Adv Drug Deliv Rev. Jul. 30, 2007;59(7):603-616.

Shah et al., "Salt Formation" in Pharmaceutical Dosage Forms: Tablets; Larry L. Augsburger et al. [Eds.]; 3rd edition, vol. 2, chapter 2, p. 62-66, Dec. 31, 2008.

Stewart et al., "Oral cephalosporin and [beta]-lactamase inhibitor combinations for ESBL-producing Enterobacteriaceae urinary tract infections". J Antimicro Chemother. Sep. 1, 2020;75(9):2384-2393.

Zhanel et al., "Cefiderocol: A siderophore cephalosporin with activity against carbapenem-resistant and multidrug-resistant gram-negative bacilli", Drugs. Feb. 28, 2019;79: 271-289.

1

BORONIC ACID DERIVATIVES AND THERAPEUTIC USES THEREOF

STATEMENT REGARDING FEDERALLY SPONSORED R&D

This invention was made with U.S. government support under the Department of Health and Human Services Contract No. HHS0100201600026C. The U.S. government has certain rights in the invention.

BACKGROUND

Field

The present application relates to the fields of chemistry and medicine. More particularly, the present application relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K. et al., Crit. Care Nurse 2008, 28, 15; Perez, F. et al., Expert Rev. Anti Infect. Ther. 2008, 6, 269; Bou, G.; Martinez-Beltran, J., Antimicrob. Agents Chemother. 2000, 40, 428. 2006, 50, 2280; Bou, G. et al., J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However, dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

In view of β-lactamase mediated resistance, new β-lactamase inhibitors (BLIs) are needed.

SUMMARY OF THE INVENTION

In some embodiments, provided herein is a crystalline form of Compound II':

(II')

-continued or a solvent thereof. In some embodiments, the crystalline form may exhibits an X-ray powder diffraction pattern comprising at least three characteristic peaks, wherein said characteristic peaks are selected from the group consisting of 4.3, 7.0, 7.2, 8.3, 11.0, 12.5, 15.0, 16.7, 17.5, 18.2, 19.1, 20.3, 22.3, 22.7, and 25.6 degrees 2θ. In some embodiments, the crystalline form of Compound II' may exhibit an X-ray powder diffraction pattern comprising at least three characteristic peaks, wherein said characteristic peaks are selected from the group consisting of 4.3, 7.0, 7.2, 8.3, 11.0, 12.5, 15.0, 16.7, 17.5, 18.2, 19.1, 20.3, 22.3, 22.7, and 25.6 degrees 2θ.

In some embodiments, the crystalline form of Compound II' may have an endotherm at about 141° C.

In some embodiments, the crystalline form may exhibits an X-ray powder diffraction pattern comprising at least three characteristic peaks, wherein said characteristic peaks are selected from the group consisting of 4.3, 7.0, 7.2, 8.3, 11.0, 12.5, 15.0, 16.7, 17.5, 18.2, 19.1, 20.3, 22.3, 22.7, and 25.6 degrees 2θ. In some embodiments, the crystalline form of Compound II' may exhibit an X-ray powder diffraction pattern comprising at least three characteristic peaks, wherein said characteristic peaks are selected from the group consisting of 4.3, 7.0, 7.2, 8.3, 11.0, 12.5, 15.0, 16.7, 17.5, 18.2, 19.1, 20.3, 22.3, 22.7, and 25.6 degrees 2θ.

In some embodiments, the crystalline form of Compound II' may have an endotherm at about 141° C.

In some embodiments, the crystalline form of Compound II' may have an endotherm at about 152° C.

In some embodiments, the crystalline form of Compound II' may be unsolvated.

In some embodiments, provided herein is a compound having the structure of or a pharmaceutically acceptable salt of any of the foregoing. In some embodiments, the pharmaceutically acceptable salt is the sodium salt.

In some embodiments provided herein is a pharmaceutical composition comprising a therapeutically effective amount of a compound described herein and a pharmaceutically acceptable excipient. In some embodiments, the composition may further comprise an additional medicament. In some embodiments, the additional medicament may be selected from the group consisting of an antibacterial agent, an antifungal agent, an antiviral agent, an anti-inflammatory agent, and an anti-allergic agent.

In some embodiments, the pharmaceutical composition may comprise a β-lactam antibacterial agent. In some embodiments, the β-lactam antibacterial agent may be selected from the group consisting of Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefidericol, Cefditoren, Cefetamet, Cefmenoxime, Cefodizime, Cefoperazone, Cefotaxime, Cefpimizole, Cefpiramide, Cefpodoxime, Cefpodoxime proxetil, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftolozane (CXA-101), RWJ-54428, MC-04,546, ME1036, Ceftiofur, Cefquinome, Cefovecin, RWJ-442831, RWJ-333441, and RWJ-333442. In other embodiments, the β-lactam antibacterial agent may be selected from the group consisting of Ceftazidime, Biapenem, Doripenem, Ertapenem, Imipenem, Meropenem, Tebipenem, Tebipenem pivoxil, Apapenem, and Panipenem. In yet other embodiments, the β-lactam antibacterial agent may be selected from the group consisting of Aztreonam, Tigemonam, BAL30072, SYN 2416, and Carumonam.

Also provided herein is method of treating a bacterial infection, comprising administering a compound described herein to a subject in need thereof. In some embodiments, the method further comprises administering to the subject an additional medicament. In some embodiments, the additional medicament may be an antibacterial agent, an antifungal agent, an antiviral agent, an anti-inflammatory agent, or an antiallergic agent. In some embodiments, the additional medicament is a β-lactam antibacterial agent. In some embodiments, the β-lactam antibacterial agent may be selected from the group consisting of Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefidericol, Cefditoren, Cefetamet, Cefmenoxime, Cefodizime, Cefoperazone, Cefotaxime, Cefpimizole, Cefpiramide, Cefpodoxime, Cefpodoxime proxetil, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftolozane (CXA-101), RWJ-54428, MC-04,546, ME1036, Ceftiofur, Cefquinome, Cefovecin, RWJ-442831, RWJ-333441, and RWJ-333442. In other embodiments, the β-lactam antibacterial agent may be selected from the group consisting of Ceftazidime, Biapenem, Doripenem, Ertapenem, Imipenem, Meropenem, Tebipenem, Tebipenem pivoxil, Apapenem, and Panipenem. In yet other embodiments, the β-lactam antibacterial agent may be selected from the group consisting of Aztreonam, Tigemonam, BAL30072, SYN 2416, and Carumonam.

In some embodiments, subject is a mammal. In some specific embodiments, the mammal is a human.

In some embodiments, the infection comprises a bacteria selected from the group consisting of *Pseudomonas acidovorans, Pseudomonas alcaligenes, Pseudomonas putida, Burkholderia cepacia, Aeromonas hydrophilia, Francisella tularensis, Morganella morganii, Proteus mirabilis, Proteus vulgaris, Providencia alcalifaciens, Providencia rettgeri, Providencia stuartii, Acinetobacter baumannii, Bordetella pertussis, Bordetella* para *pertussis, Bordetella bronchiseptica, Haemophilus ducreyi, Pasteurella multocida, Pasteurella haemolytica, Branhamella catarrhalis, Borrelia burgdorferi, Kingella, Gardnerella vaginalis, Bacteroides distasonis, Bacteroides* 3452A homology group, *Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*. In other embodiments, the infection comprises a bacteria selected from the group consisting of *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae,*

*Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, and *Bacteroides splanchnicus.*

Also provided herein is a method of preparing crystalline Form A of Compound II', the method comprising the steps of: dissolving Compound II' in a solvent system to form a crystallization solution, wherein the solvent system consists of isopropyl acetate; heating the crystallization solution to about 50° C.; adding heptane to the crystallization solution; and adding seed crystals of crystalline Form A of Compound II' to the crystallization solution.

Also provided herein is a method of preparing crystalline Form A of Compound II', the method comprising the steps of: dissolving Compound II' in a solvent system to form a crystallization solution, wherein the solvent system consists of isopropyl acetate and isopropanol; adding heptane to the crystallization solution; and adding seed crystals of crystalline Form B of Compound II' to the crystallization solution. In some embodiments, the solvent system consists of isopropyl acetate and isopropanol in a 1:1 (v/v) ratio.

Also provided herein is a method of preparing crystalline Form A of Compound II', the method comprising the steps of: dissolving Compound II' in a solvent system to form a crystallization solution, wherein the solvent system consists of isopropyl acetate; heating the crystallization solution; adding heptane to the crystallization solution; and adding seed crystals of crystalline Form A of Compound II' to the crystallization solution.

In some embodiments, the crystallization solution may be heated to a temperature of 30 to 80° C. In other embodiments, the crystallization solution may be heated to a temperature of 40 to 70° C. In some embodiments, the crystallization solution may be heated to a temperature of 50° C.

Also provided herein is a method of preparing crystalline Form B of Compound II', the method comprising the steps of: dissolving Compound II' in a solvent system to form a crystallization solution, wherein the solvent system consists of isopropyl acetate and isopropanol; adding heptane to the crystallization solution; and adding seed crystals of crystalline Form B of Compound II' to the crystallization solution. In some embodiments, the solvent system may consist of isopropyl acetate and isopropanol in a 1:1 (v/v) ratio.

Also provided herein is a method of preparing crystalline Form A of Compound II', the method comprising the steps of: dissolving Compound II' in a solvent system to form a crystallization solution, wherein the solvent system consists of hexanes and ethyl acetate; heating the crystallization solution; initially cooling the crystallization solution; stirring the crystallization solution; further cooling the crystallization solution to room temperature; and allowing the crystallization mixture to stand at room temperature.

In some embodiments, the crystallization solution may be heated to a temperature of 30 to 80° C. In other embodiments, the crystallization solution may be heated to a temperature of 50 to 70° C. In some embodiments, the crystallization solution may heated to a temperature of 65° C.

In some embodiments, the crystallization solution may initially be cooled to a temperature of 30 to 50° C. In some embodiments, the crystallization solution may initially be cooled to a temperature of 50° C.

In some embodiments, the crystallization solution may further be stirred for 12 to 36 hours. In some specific embodiments, the crystallization solution may further be stirred for 24 hours. In some embodiments, the crystallization solution may further be allowed to stand at room temperature for 72 hours.

In some embodiments provided herein is a method of preparing crystalline Form A of Compound II', the method comprising the steps of: dissolving Compound II' in isopropanol to form a crystallization solution; heating the crystallization solution; and cooling the crystallization solution to room temperature.

In another embodiment, provided herein is a method of preparing Compound II' comprising the steps of: combining Compound I, or a salt thereof, a halomethyl isobutyrate, and a base in a polar organic solvent to form a reaction mixture; and heating the reaction mixture.

In some embodiments, the reaction mixture may further comprise an iodide source. In some specific embodiments, the iodide source may be sodium iodide, potassium iodide, or cesium iodide.

In some embodiments, the base may be $NaH_2PO_4$. In other embodiments, the base may be $Na_2B_4O_7$.

In some embodiments, the molar ratio of base to Compound I may be from about 0.5 to about 2.0. In some embodiments, the molar ratio of base to Compound I may be 1.0. In other embodiments, the molar ratio of base to Compound I may be 1.5.

In some embodiments, the solvent may be acetonitrile. In some specific embodiments, the acetonitrile may be anhydrous.

In some embodiments, the halomethyl isobutyrate may be chloromethyl isobutyrate.

In some embodiments, the reaction mixture may be heated to a temperature of from about 50° C. to about 80° C. In some embodiments, the reaction mixture may be heated to a temperature of 60° C. In other embodiments, the reaction mixture may be heated to a temperature of 70° C. In yet other embodiments, the reaction mixture may heated to a temperature of 80° C.

In some embodiments, the reaction mixture may be heated for a period of from about 0.5 hours to about 24 hours. In some embodiments, the reaction mixture may be heated for a period of from about 4 hours to about 18 hours. In some embodiments, the reaction mixture may be heated for 6 hours. In other embodiments, the reaction mixture may be heated for 8 hours. In some embodiments, the reaction mixture may be heated for 16 hours.

DETAILED DESCRIPTION OF EMBODIMENTS

Figure 1:
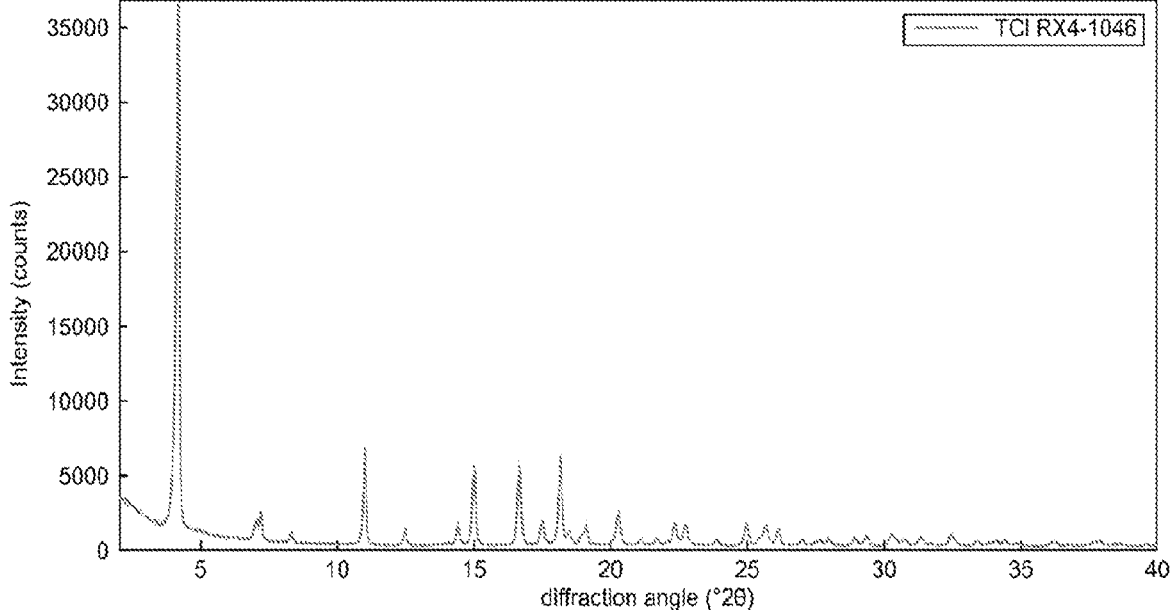
FIG. 1 is an X-ray powder diffraction pattern of crystalline Form A of Compound II'.

Compound I and pharmaceutically acceptable salts thereof are described in International Application PCT/US2017/039787, which is incorporated herein by reference in its entirety. Compound I is a β-lactamase inhibitor effective in treating bacterial infections when used in combination with β-lactam antibiotics.

Compound I

Disclosed herein is a Compound II, a prodrug of Compound I. Compound II is a β-lactamase inhibitor effective in treating bacterial infections when used in combination with β-lactam antibiotics.

Compound II

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Synthesis of Compound II

Compound II and pharmaceutically acceptable salts thereof may be prepared from Compound I, or a salt thereof by treatment with chloromethyl isobutyrate under basic conditions. General methods for preparing (isobutyryloxy) methyl esters are described in International Patent Publication No. WO 2018/005662, which is incorporated herein by reference in its entirety. The synthesis of Compound II is provided in the Examples below. In some embodiments, the sodium salt of Compound II (Compound II') may be formed.

Compound II'

In some embodiments, Compound II' may be prepared from Compound I, or a salt thereof, according to the scheme below. Compound I, or a salt thereof, can be treated with a halomethyl isobutyrate in the presence of base and an optional iodidie source in order to form Compound II'

In some embodiments, an excess of halomethyl isobutyrate is used in the reaction. For example, in some embodiments, 1.0, 1.5, 2.0, 2.5, 3.0, 3.5, 4.0, 4.5, 5.0 or more molar equivalents of halomethyl isobutyrate relative to Compound I may be used for this reaction. In some embodiments, the halomethyl isobutyrate may be chloromethyl isobutyrate. In other embodiments, the halomethyl isobutyrate may be bromomethyl isobutyrate.

In some embodiments, the iodide source may be an alkali metal iodide. For example, the iodide source may be sodium iodide, potassium iodide, or cesium iodide.

The selection of base used in the reaction may affect the overall yield and purity of the final product. In some embodiments, the base may be sodium bicarbonate. In other embodiments, the base may be $NaH_2PO_4$. In yet other embodiments, the base may be $Na_2B_4O_7$. In some specific embodiments, the base may be anhydrous $Na_2B_4O_7$. In some embodiments, 0.1 to 10 molar equivalents of base relative to Compound I can be used for this reaction. For example, the number of molar equivalents of base relative to Compound I may be 0.1, 0.2, 0.3. 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0, or within a range defined by the aforementioned values. In some specific embodiments, 0.5 to 2.0 molar equivalents of base relative to Compound I may be used in the reaction.

The reaction for converting Compound I' or a salt thereof to Compound II' may be conducted in a variety of solvents. In some embodiments, the solvent may be a polar aprotic solvent. In some embodiments, the solvent may be acetonitrile, dimethylformamide, methylene chloride, chloroform, tetrahydrofuran, 2-methyltetrahydrofuran, diethyl ether, methyl tert butyl ether, N-methylpyrrolidinone, acetone, methyl ethyl ketone, or any combination of the aforementioned solvents. In some embodiments, the solvent may be anhydrous. In some embodiments, the solvent may be acetonitrile.

The reaction for converting Compound I' or a salt thereof to Compound II' may be conducted at a variety of temperatures. In some embodiments, the reaction temperature is from about 25° C. to about 100° C., from about about 30° C. to about 90° C., from about 40° C. to about 80° C., from about 50° C. to about 80° C., from about 55° C. to about 80° C., from about 60° C. to about 80° C., from about about 65° C. to about 80° C., or from about 70° C. to about 80° C. For instance, in some embodiments, the reaction for converting Compound I' or a salt thereof to Compound II' may be conducted at 25° C., 30° C., 35° C., 40° C., 45° C., 50° C., 55° C., 60° C., 65° C., 70° C., 75° C., 80° C., 85° C., 90° C., 95° C., 100° C., or higher. In some embodiments, the reaction may be heated at any of the aforementioned temperatures for 0.5 hour, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more.

Crystalline Forms of Compound II'

Disclosed herein are crystalline forms of Compound II'. Two forms, Form A and Form B have been identified (described below).

Crystalline Form A of Compound II'

Some embodiments include a crystalline form of Compound II', referred to herein as crystalline Form A. The precise conditions for forming crystalline Form A of Compound II' may be empirically determined and it is only possible to give a number of methods which have been found to be suitable in practice.

Crystalline Form A of Compound II' was characterized using various techniques which are described in further detail in the experimental methods section. FIG. 1 shows the crystalline structure of Form A of Compound II' as determined by X-ray powder diffraction (XRPD). Crystalline Form B of Compound II', which may be obtained by the methods disclosed herein, exhibits prominent peaks at approximately 4.3, 7.0, 7.2, 8.3, 11.0, 12.5, 15.0, 16.7, 17.5, 18.2, 19.1, 20.3, 22.3, 22.7, and 25.6 degrees 2θ. Thus, in some embodiments, a crystalline form of Compound II' has at least one characteristic peak (e.g., one, two, three, four, five, six, seven, eight, nine, ten, eleven, twelve, thirteen, fourteen, or fifteen characteristic peaks) selected from approximately 4.3, 7.0, 7.2, 8.3, 11.0, 12.5, 15.0, 16.7, 17.5, 18.2, 19.1, 20.3, 22.3, 22.7, and 25.6 degrees 2θ. In some embodiments, a crystalline form of Compound II' has at least three characteristic peaks selected from approximately 4.3, 7.0, 7.2, 8.3, 11.0, 12.5, 15.0, 16.7, 17.5, 18.2, 19.1, 20.3, 22.3, 22.7, and 25.6 degrees 2θ.

Figure 2:
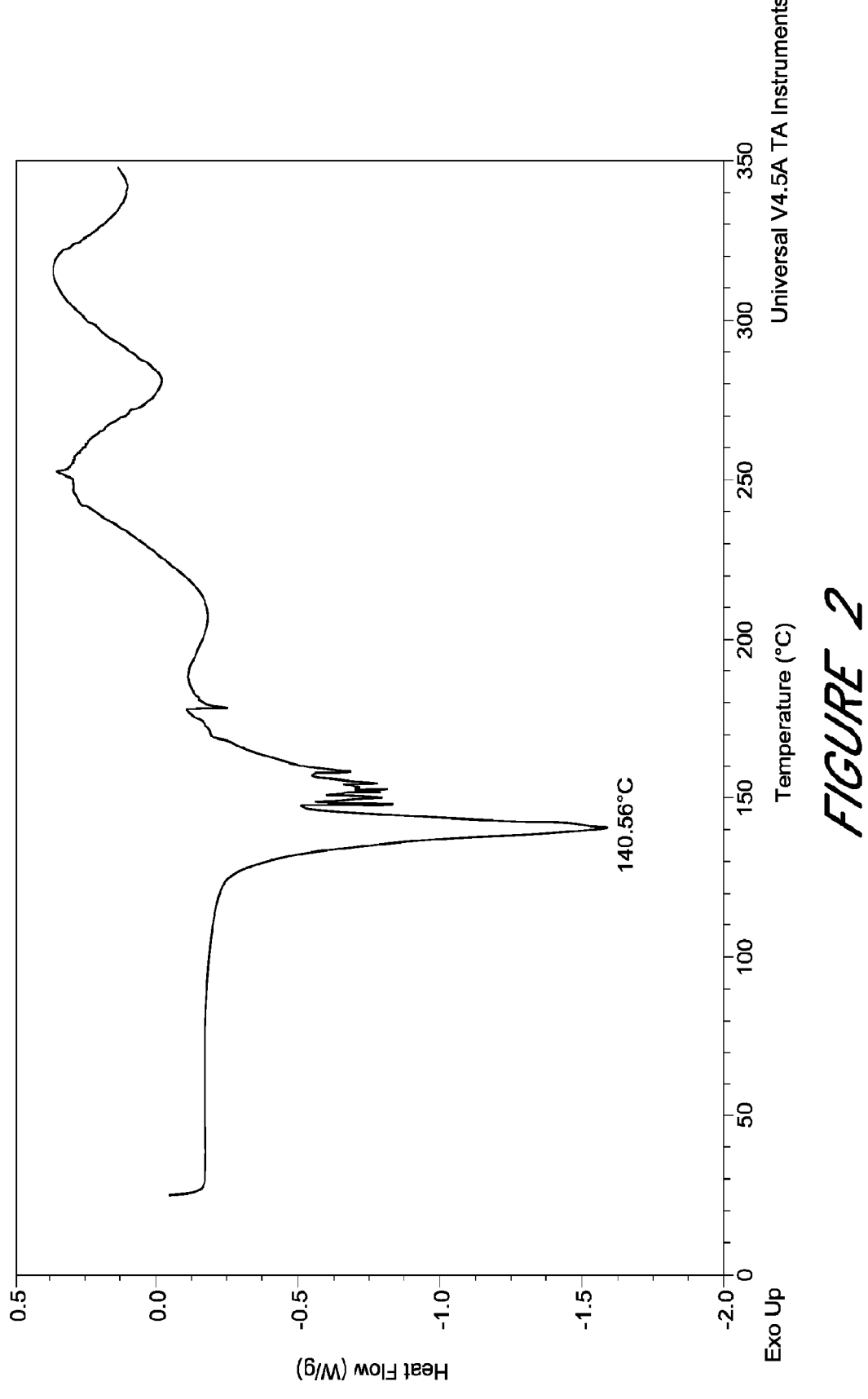
FIG. 2 shows a differential scanning calorimetry analysis for crystalline Form A of Compound II'.

FIG. 2 shows results obtained by differential scanning calorimetry (DSC) for crystalline Form A of Compound II'. The DSC results show a peak at temperature of about 141° C., which indicates the melting point for the crystal. Accordingly, in some embodiments, crystalline Form B of Compound II' exhibits a melting point from about 138° C. to about 144° C., from about 139° C. to about 143° C., or at about 141° C.

Figure 3:
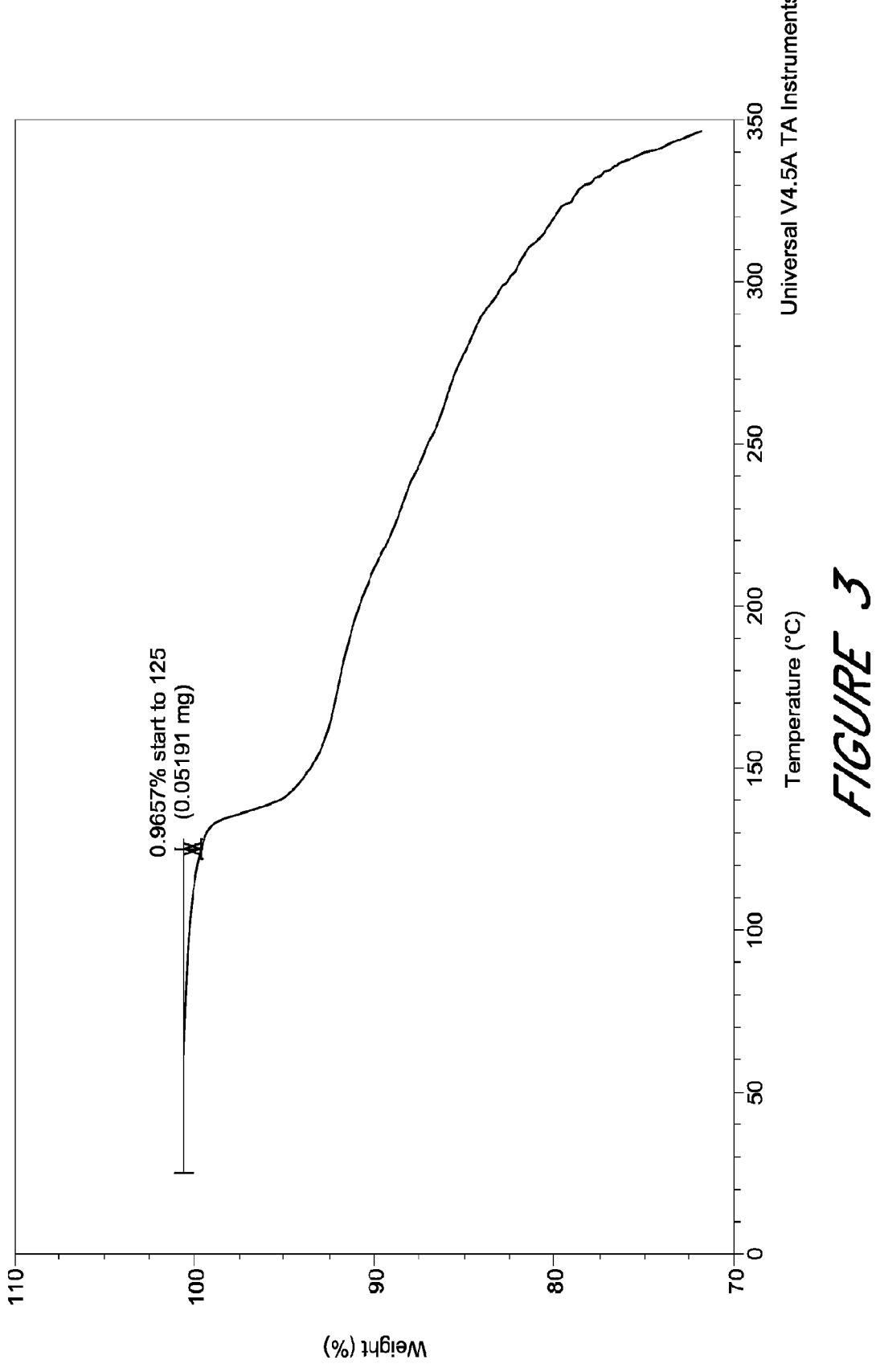
FIG. 3 shows thermogravimetric analysis results for crystalline Form A of Compound II'.
Figure 4:
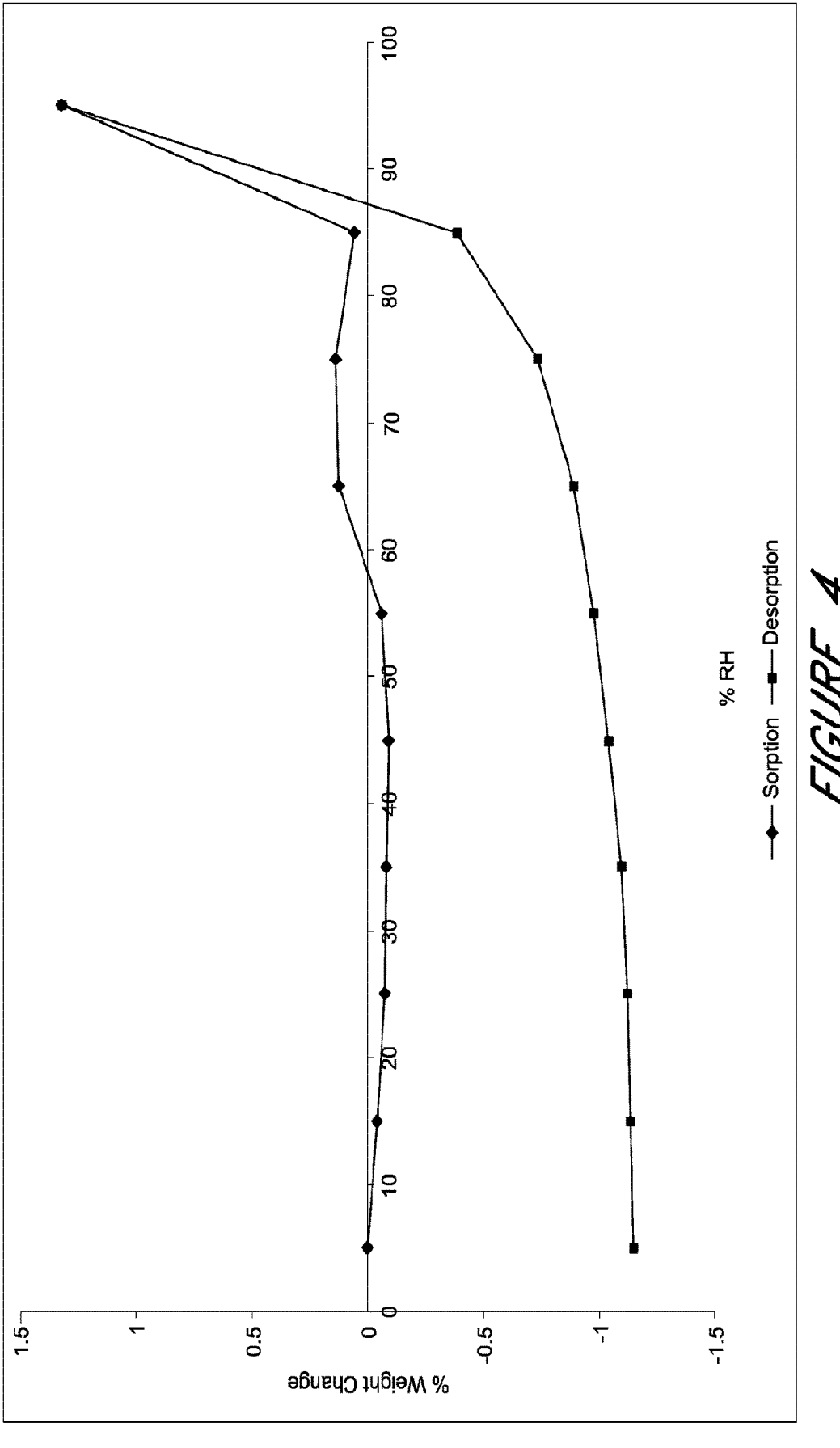
FIG. 4 shows dynamic vapor sorption results for crystalline Form A of Compound II'.

FIG. 3 shows results obtained by thermogravimetric analysis (TGA) for crystalline Form A of Compound II'. The TGA results show that crystalline Form A of Compound II' exhibited about a 1% weight loss when carried from 25° C. to 125° C. Meanwhile, FIG. 4 shows dynamic vapor sorption (DVS) results for crystalline Form A of Compound II', and shows slight water uptake and indicates that crystalline Form A of Compound II' is slightly hygroscopic. Karl Fisher analysis indicates that crystalline Form A of Compound II' contains, on average, 0.12% water, indicating that crystalline Form A of Compound II' is unsolvated. Elemental analysis of crystalline Form A of Compound II' is consistent with anhydrous material.

Figure 5:
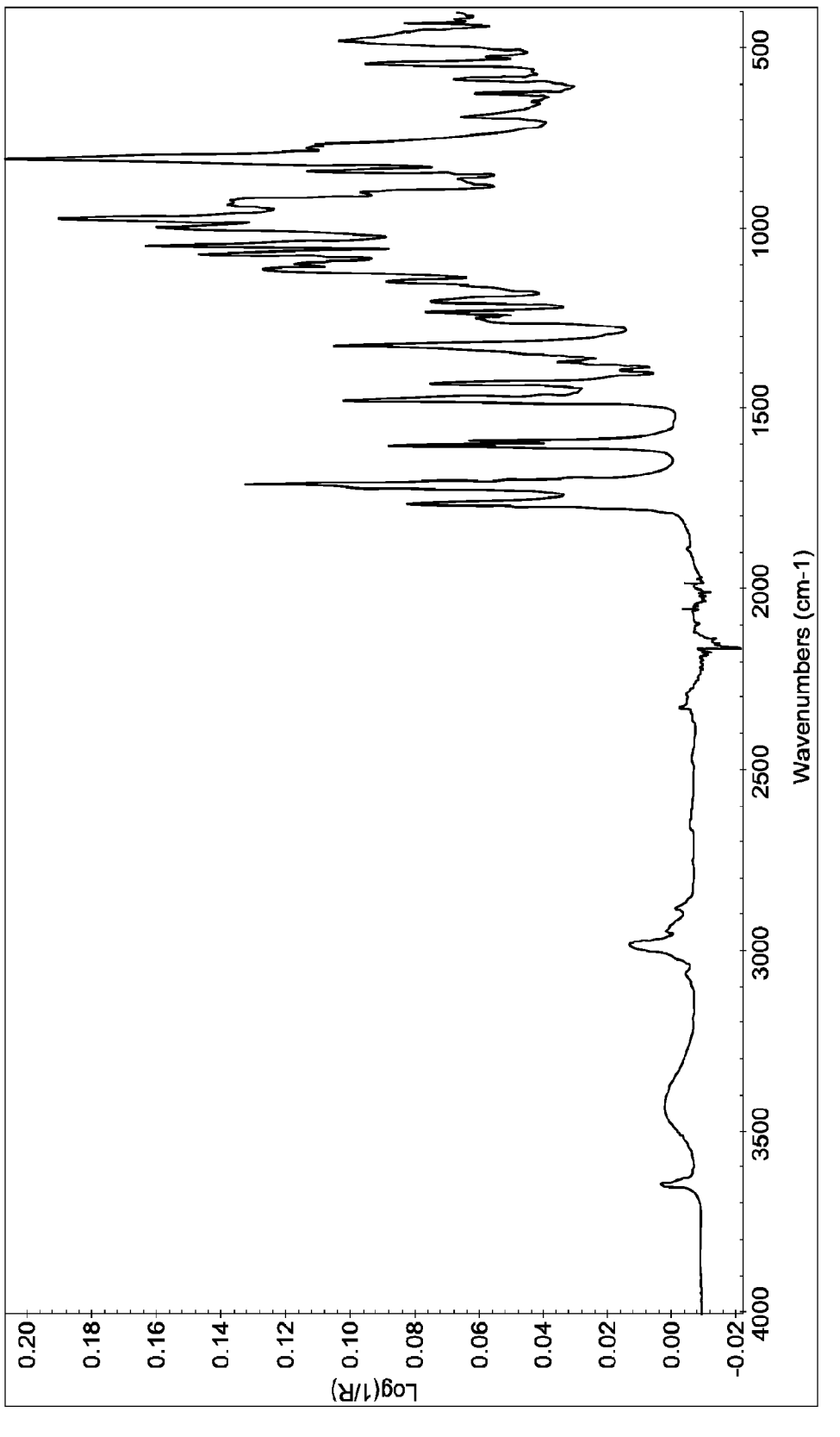
FIG. 5 shows results obtained by FTIR spectroscopy for crystalline Form B of Compound II'.

FIG. 5 shows results obtained by Fourier Transform Infrared (FTIR) spectroscopy for crystalline Form A of Compound II'. Crystalline Form A of Compound II' exhibits prominent peaks at approximately 1758, 1706, 1600, 1584, 1469, 1426, 1389, 1366, and 1322 cm⁻¹. Thus, in some embodiments, a crystalline form of Compound II' has at least one characteristic FTIR peak (e.g., one, two, three, four, five, six, seven, eight, or nine characteristic peaks) selected from approximately 1758, 1706, 1600, 1584, 1469, 1426, 1389, 1366, and 1322 cm⁻¹. In some embodiments, a crystalline form of Compound II' has at least three characteristic peaks selected from 1758, 1706, 1600, 1584, 1469, 1426, 1389, 1366, and 1322 cm⁻¹. In some embodiments, peak positions recited herein include variability within ±1 cm⁻¹.

Figure 6:
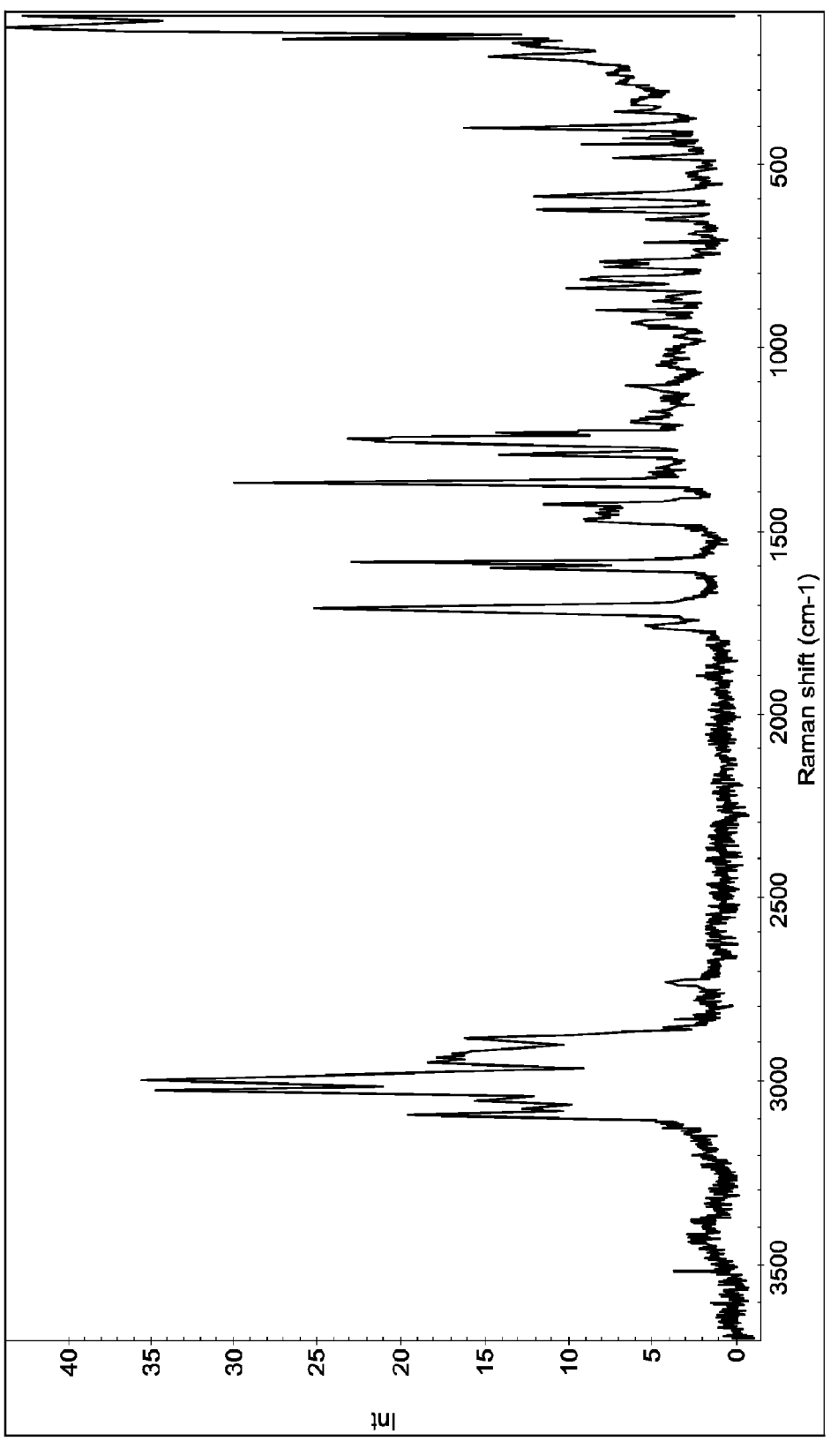
FIG. 6 shows results obtained by FT Raman spectroscopy for crystalline Form B of Compound II'.

FIG. 6 shows results obtained by Fourier Transform Raman spectroscopy for crystalline Form B of Compound II'. Crystalline Form A of Compound II' exhibits prominent peaks at approximately 1754, 1709, 1600, 1584, 1465, 1428, 1366, and 1340 cm⁻¹. Thus, in some embodiments, a crystalline form of Compound II' has at least one characteristic FT Raman peak (e.g., one, two, three, four, five, six, seven, or eight characteristic peaks) selected from approximately 1754, 1709, 1600, 1584, 1465, 1428, 1366, and 1340 cm⁻¹. In some embodiments, a crystalline form of Compound II' has at least three characteristic peaks selected from 1754, 1709, 1600, 1584, 1465, 1428, 1366, and 1340 cm⁻¹. In some embodiments, peak positions recited herein include variability within +2 cm⁻¹.

Figure 7:
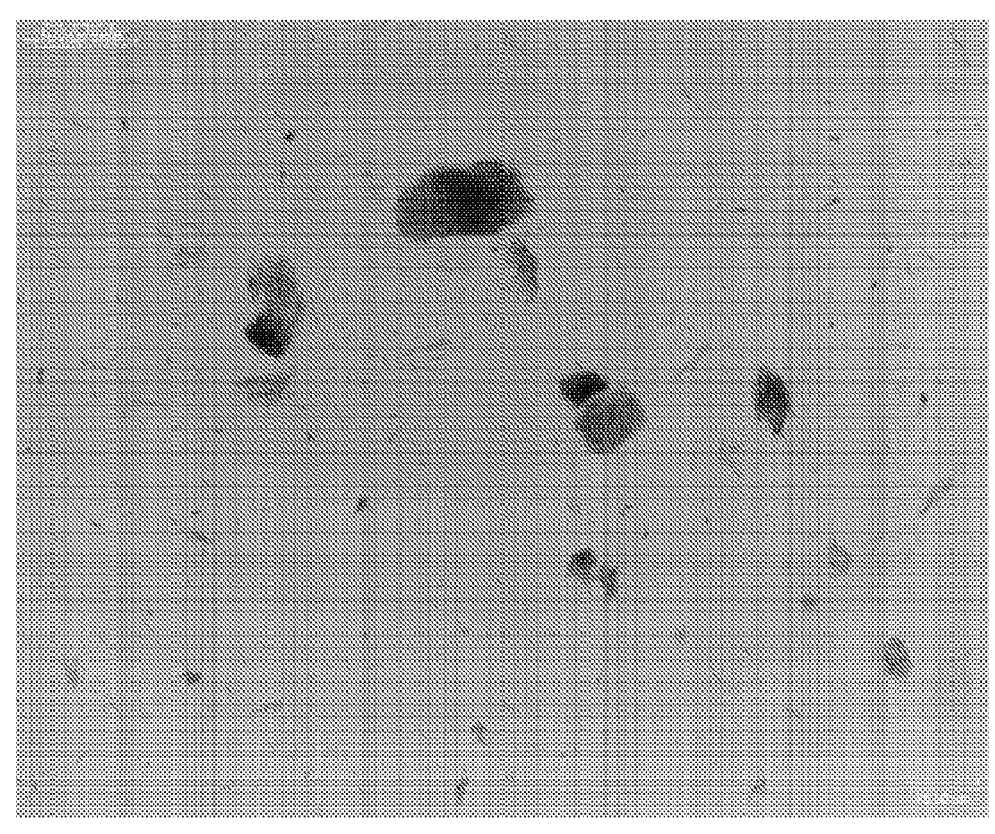
FIG. 7 shows an optical microscopy image of crystals of crystalline Form B of Compound II'.

Crystalline Form A of Compound II' can therefore be characterized as an unsolvated, slightly hygroscopic solid. Crystal Form A of Compound II' also shows good crystallinity with needle shaped crystals of varying size (FIG. 7) and a relatively high melting point (approximately 141° C.).

Crystalline Form B of Compound II'

Some embodiments include a crystalline form of Compound II', referred to herein as crystalline Form B. The precise conditions for forming crystalline Form B of Compound II' may be empirically determined and it is only possible to give a number of methods which have been found to be suitable in practice.

Figure 8:
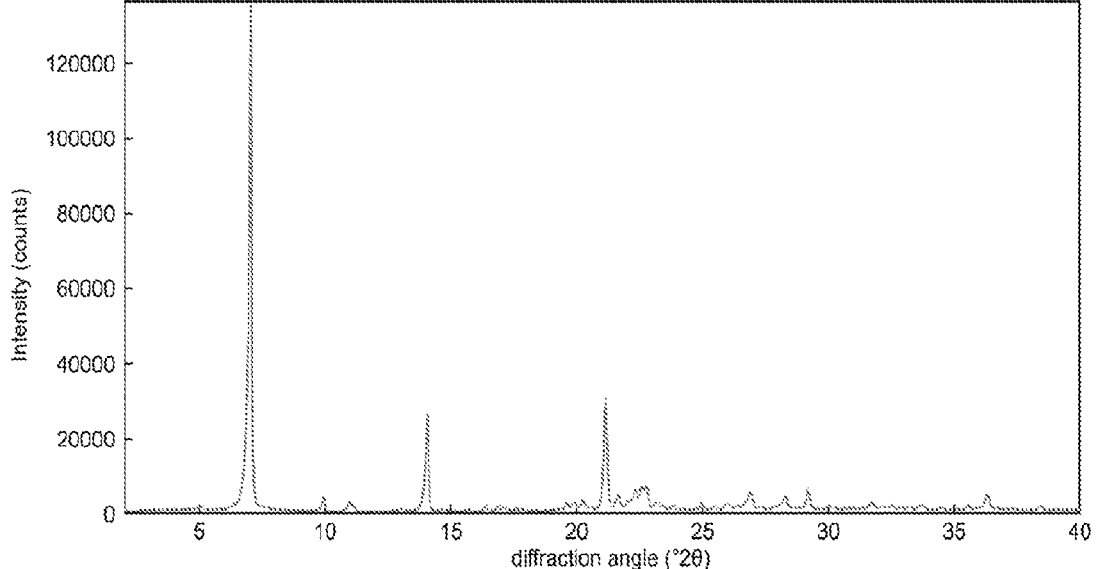
FIG. 8 is an X-ray powder diffraction pattern of crystalline Form B of Compound II'.

Crystalline Form B of Compound II' was characterized using various techniques which are described in further detail in the experimental methods section. FIG. 8 shows the crystalline structure of Form B of Compound II' as determined by X-ray powder diffraction (XRPD). Crystalline Form B of Compound II', which may be obtained by the methods disclosed herein, exhibits prominent peaks at approximately 5.1, 7.0, 9.9, 11.0, 11.1, 14.1, 16.4, 17.1, 21.1, 22.3, 22.6, 26.9, and 28.3 degrees 2θ. Thus, in some embodiments, a crystalline form of Compound II' has at least one characteristic peak (e.g., one, two, three, four, five, six, seven, eight, nine, ten, eleven, twelve, or thirteen characteristic peaks) selected from approximately 5.1, 7.0, 9.9, 11.0, 11.1, 14.1, 16.4, 17.1, 21.1, 22.3, 22.6, 26.9, and 28.3 degrees 2θ. In some embodiments, a crystalline form of Compound II' has at least three characteristic peaks selected from approximately 5.1, 7.0, 9.9, 11.0, 11.1, 14.1, 16.4, 17.1, 21.1, 22.3, 22.6, 26.9, and 28.3 degrees 2θ.

Figure 9:
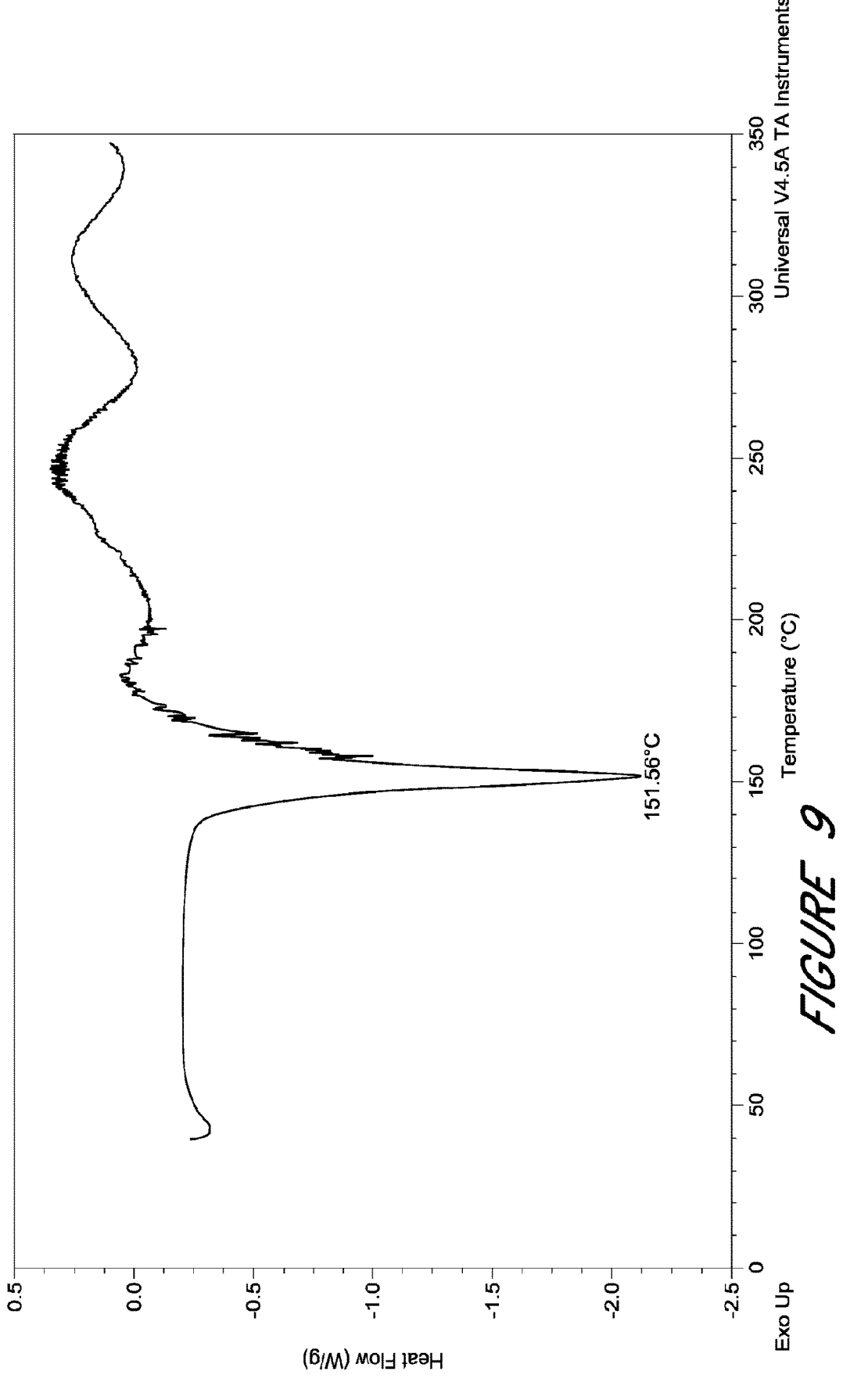
FIG. 9 shows a differential scanning calorimetry analysis for crystalline Form B of Compound II'.

FIG. 9 shows results obtained by differential scanning calorimetry (DSC) for crystalline Form B of Compound II'. The DSC results show a peak at temperature of about 152° C., which indicates the melting point for the crystal. Accordingly, in some embodiments, crystalline Form B of Compound II' exhibits a melting point from about 149° C. to about 155° C., from about 150° C. to about 154° C., or at about 152° C.

Figure 10:
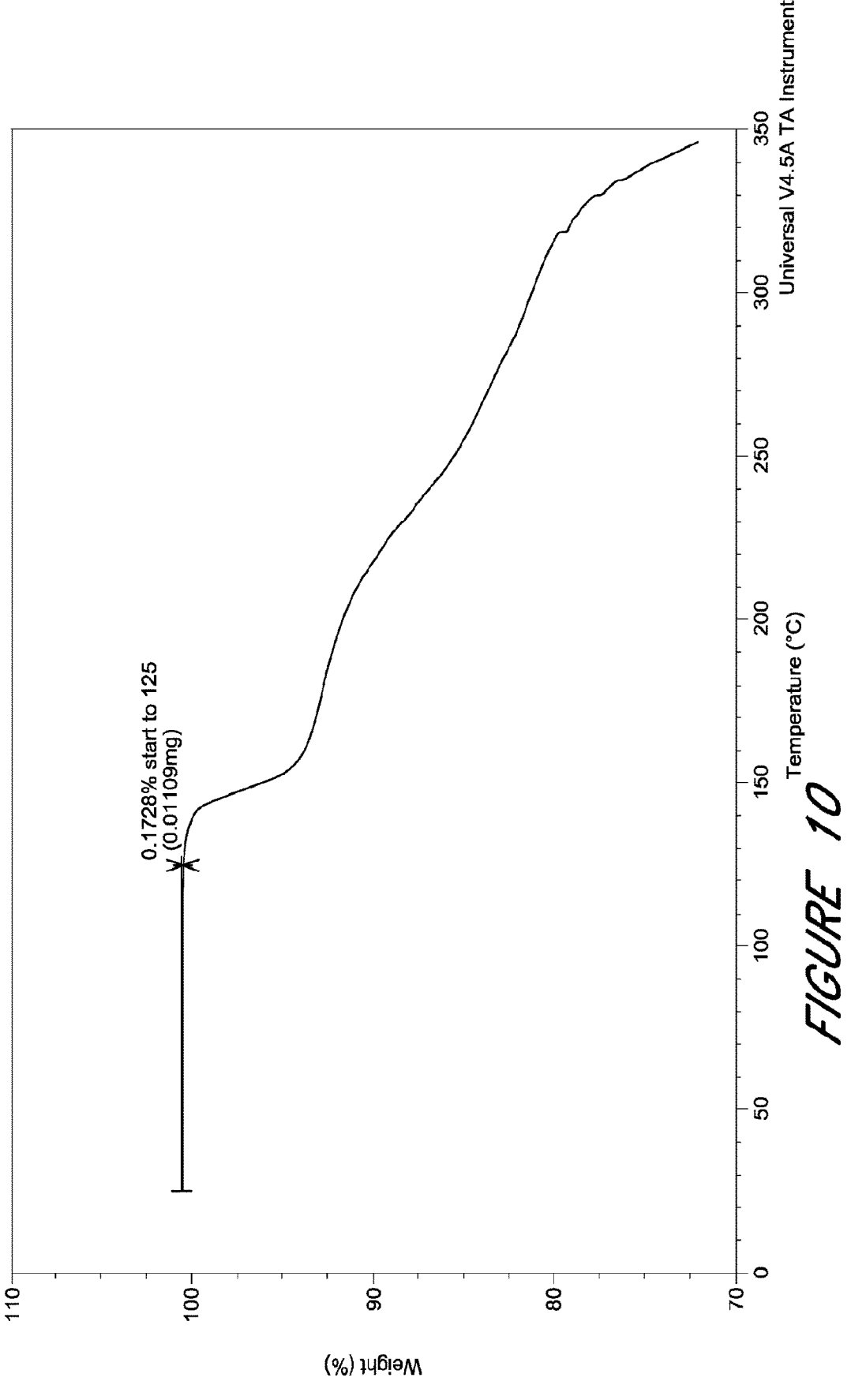
FIG. 10 shows thermogravimetric analysis results for crystalline Form B of Compound II'.
Figure 11:
FIG. 11 shows dynamic vapor sorption results for crystalline Form B of Compound II'.

FIG. 10 shows results obtained by thermogravimetric analysis (TGA) for crystalline Form B of Compound II'. The TGA results show that crystalline Form B of Compound II' exhibited a 0.18% weight loss when carried from 25° C. to 125° C. Meanwhile, FIG. 11 shows dynamic vapor sorption (DVS) results for crystalline Form B of Compound II', and shows moderate water uptake and indicates that crystalline Form B of Compound II' is moderately hygroscopic. Karl Fisher analysis indicates that crystalline Form B of Compound II' contains, on average, 7.29% water. However, the water is believed to be a decomposition product from heating the sample. Elemental analysis shows crystalline Form B of Compound II' is an unsolvated material.

Figure 12:
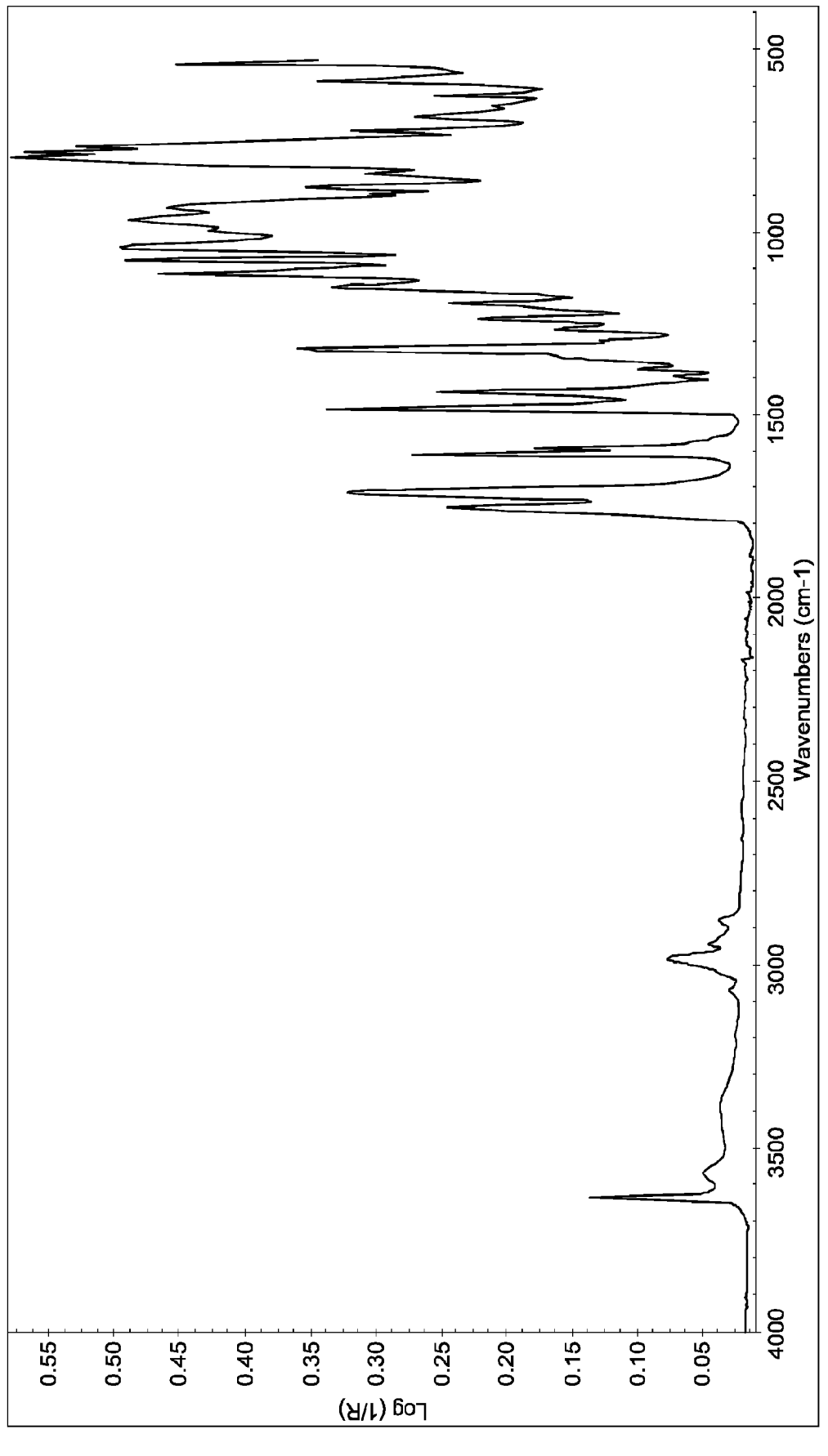
FIG. 12 shows results obtained by FTIR spectroscopy for crystalline Form B of Compound II'.

FIG. 12 shows results obtained by Fourier Transform Infrared (FTIR) spectroscopy for crystalline Form B of Compound II'. Crystalline Form B of Compound II' exhibits prominent peaks at approximately 1608, 1592, 1553, 1473, 1416, 1364, 1334, and 1277 cm⁻¹. Thus, in some embodiments, a crystalline form of Compound II' has at least one characteristic FTIR peak (e.g., one, two, three, four, five, six, seven, or eight characteristic peaks) selected from approximately 1608, 1592, 1553, 1473, 1416, 1364, 1334, and 1277 cm⁻¹. In some embodiments, a crystalline form of Compound II' has at least three characteristic peaks selected from 1608, 1592, 1553, 1473, 1416, 1364, 1334, and 1277 cm$^{-1}$. In some embodiments, peak positions recited herein include variability within ±1 cm$^{-1}$.

Figure 13:
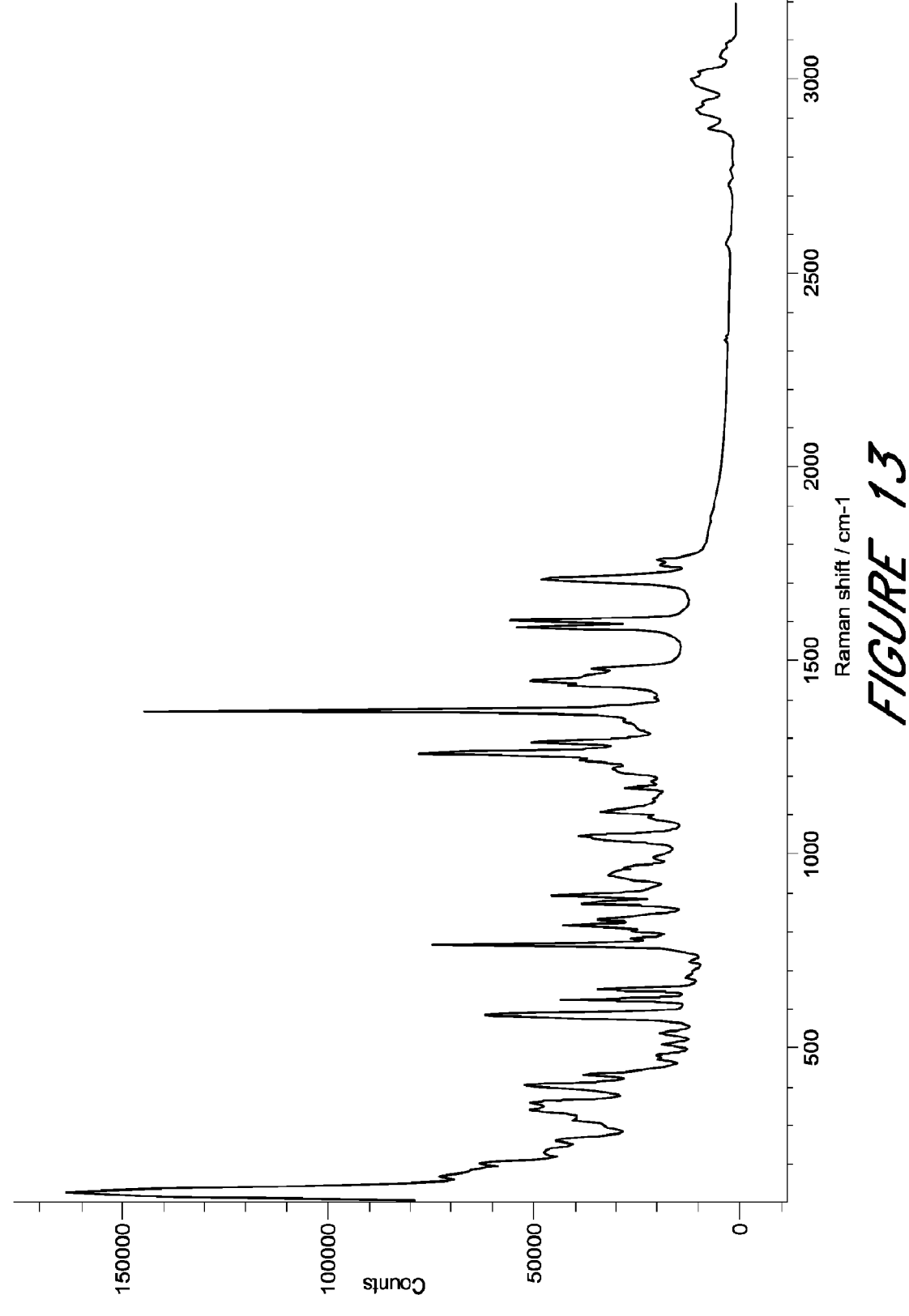
FIG. 13 shows results obtained by FT Raman spectroscopy for crystalline Form B of Compound II'.

FIG. 13 shows results obtained by Fourier Transform Raman spectroscopy for crystalline Form B of Compound II'. Crystalline Form B of Compound II' exhibits prominent peaks at approximately 1611, 1591, 1574, 1472, 1426, and 1366 cm$^{-1}$. Thus, in some embodiments, a crystalline form of Compound II' has at least one characteristic FT Raman peak (e.g., one, two, three, four, five, or six characteristic peaks) selected from approximately 1611, 1591, 1574, 1472, 1426, and 1366 cm$^1$. In some embodiments, a crystalline form of Compound II' has at least three characteristic peaks selected from 1611, 1591, 1574, 1472, 1426, and 1366 cm$^{-1}$. In some embodiments, peak positions recited herein include variability within ±2 cm$^{-1}$.

Figure 14:
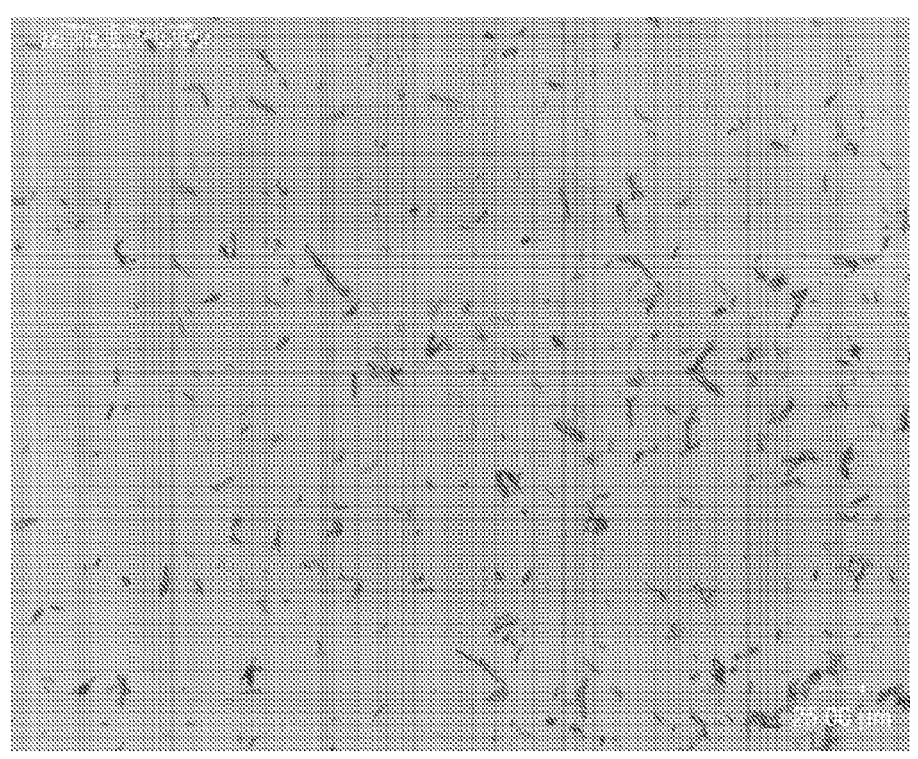
FIG. 14 shows an optical microscopy image of crystals of crystalline Form B of Compound II'.

Crystalline Form B of Compound II' can therefore be characterized as an unsolvated, moderately hygroscopic solid. Crystal Form B of Compound II' also shows good crystallinity with blade shaped crystals of varying size (FIG. 14) and a relatively high melting point (approximately 152° C.).

Methods of Crystalizing Compound II'

Disclosed are methods of crystalizing Compound II'. Crystalline forms of Compound II' may generally be obtained or produced by crystallizing the compound of Compound II' under controlled conditions. In some embodiments, the method may produce an unsolvated crystalline form. In some embodiments, the method may produce the crystalline Form A of Compound II'. In some embodiments, the method may produce the crystalline Form B of Compound II'.

In some embodiments, crystalline forms of Compound II' may be prepared by taking up Compound II' in a solvent to form a crystallization solution, optionally heating the first solution, and optionally adding a second solvent to the crystallization solution. In some embodiments, the first solvent may be isopropyl acetate. In other embodiments, the first solvent may be isopropyl alcohol. In other embodiments, the first solvent may be hexanes. In yet still other embodiments, the first solvent may be heptane. In some embodiments, the first solvent may be ethyl acetate. In some embodiments, the first solvent may be a combination of any of isopropyl acetate, isopropyl alcohol, hexanes, heptane, and/or ethyl acetate. In some specific embodiments, the first solvent may be a combination of isopropyl acetate and isopropyl alcohol. In other specific embodiments, the first solvent may be a combination of hexanes and ethyl acetate.

In some embodiments, the crystallization solution may optionally be heated to 30, 35, 40, 45, 50, 55, 60, 65, 70, 75, 80, 85, or 90° C., or within a range defined by any of the aforementioned temperatures.

In some embodiments, the second solvent may be heptane. In other embodiments, the second solvent may be hexanes.

In some embodiments, seeds of the desired crystalline form of Compound II' may optionally be added to the crystallization solution to facilitate crystallization.

In some embodiments, the crystallization solution may be cooled to 55, 50, 45, 40, 35, 30, 35, 20, 15, 10, 5, 0–5, or −10° C., or within a range defined by any of the aforementioned temperatures. The crystallization solution may be cooled for a period of 1, 2, 3, 4, 6, 8, 12, 16, 24, 36, 48, or 72 hours, or within a range defined by any of the aforementioned times. The cooling may be accomplished with or without stirring or agitation.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as Li$^+$, Na$^+$, K$^+$, Mg$^{2+}$ and Ca$^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

Administration and Pharmaceutical Compositions

The compounds disclosed herein are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered intravenous (i.v.).

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefidericol, Cefditoren, Cefetamet, Cefmenoxime, Cefodizime, Cefoperazone, Cefotaxime, Cefpimizole, Cefpiramide, Cefpodoxime, Cefpodoxime proxetil, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem, Tebipenem, Tebipenem pivoxil, Apapenem, and Panipenem.

Additional preferred embodiments include β-lactams such as Aztreonam, Tigemonam, and Carumonam.

Further preferred embodiments include β-lactam antibacterial agent such as tebipenem pivoxil.

Yet further preferred embodiments include β-lactam antibacterial agent such as ceftibuten.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi: 10.1128/AAC0.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vul-*

*garis, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

X-ray Powder Diffraction (XRPD)

The Rigaku Smart-Lab X-ray diffraction system was configured for reflection Bragg-Brentano geometry using a line source X-ray beam. The x-ray source was a Cu Long Fine Focus tube that was operated at 40 kV and 44 ma. That source provides an incident beam profile at the sample that changes from a narrow line at high angles to a broad rectangle at low angles. Beam conditioning slits were used on the line X-ray source to ensure that the maximum beam size was less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam was controlled by 5.0-degree Soller slits in both the incident and diffracted beam paths. The instrument was qualified using ASTM silicon standard on the same day of the analysis.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

Differential Scanning calorimetry (DSC)

DSC analyses were carried out using a TA Instruments Q2500 Discovery Series instrument. The instrument temperature calibration was performed using indium. The DSC cell was kept under a nitrogen purge of ~50 mL per minute during each analysis. The sample was placed in a standard, crimped, aluminum pan and was heated from approximately 25° C. to 350° C. at a rate of 10° C. per minute.

Melt Point (MP) Analysis

Melt point analysis was carried out using a Stuart SMP3 melt point apparatus. The sample was placed in a glass capillary and heated at 10° C. per minute.

Thermogravimetric (TG) Analysis

TG analysis was carried out using a TA Instruments Q5500 Discovery Series instrument. The instrument balance was calibrated using class M weights and the temperature calibration was performed using alumel. The nitrogen purge was −40 mL per minute at the balance and −60 mL per minute at the furnace. Each sample was placed into a pre-tared platinum pan and heated from approximately 25° C. to 350° C. at a rate of 10° C. per minute.

Dynamic Vapor Sorption (DVS) Analysis

DVS analysis was carried out using a TA Instruments Q5000 Dynamic Vapor Sorption analyzer. The instrument was calibrated with standard weights and a sodium bromide standard for humidity. Approximately 20 mg of sample was loaded into a metal-coated quartz pan for analysis. The sample was analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion was not met, after one hour. The percent weight change values were calculated using Microsoft Excel®. The temperature for the DVS analysis can impact the outcome of the results.

Karl Fischer (KF) Analyses

Karl Fischer analyses were carried out using a Mettler-Toledo C20 Coulometric KF titrator with oven attachment heated at 175° C. The instrument was calibrated using a Hydranal water standard containing 1% water. The titrant was a Hydranal methanol solution. The sample was analyzed in triplicate.

Optical Microscopy

Optical microscopy experiments were carried out on a Leica DM 2500 P compound microscope with a 10× magnification eye piece and a 10× magnification objective, for a total magnification of 100×. Images were captured using a QImaging MicroPublisher 3.3 RTV camera.

Infrared (IR) Spectroscopy

The IR spectra were obtained using a Thermo Nicolet model 6700 Fourier-transform (FT) IR spectrophotometer equipped with a deuterated triglycine sulfate (DTGS) detector, a potassium bromide (KBr) beamsplitter, and an electronically temperature controlled (ETC) Ever-Glo® IR source. The instrument was configured with a SMART iTR diamond attenuated total reflectance (ATR) sampling accessory. The single beam scan of the background (air) and sample were collected with 128 signal-averaged scans at a resolution of 2 cm⁻¹ over the spectral range 4000-400 cm⁻¹. The final sample spectrum was automatically calculated and presented in Log 1/R units. The wavelength calibration was verified using a certified polystyrene standard. Data collection and processing was performed using Omnic 9.7.46 software.

Raman Spectroscopy

Fourier transform (FT) Raman spectra were acquired on a Nicolet model 6700 spectrometer interfaced to a Nexus Raman accessory module. This instrument is configured with a Nd:YAG laser operating at 1024 nm, a $CaF_2$ beamsplitter, and a indium gallium arsenide detector. OMNIC 8.1 software was used for control of data acquisition and processing of the spectra. Samples were packed into a 3-inch glass NMR tube for analysis.

Low-Frequency Raman Spectroscopy

Raman spectroscopy is a complementary technique to infrared (IR) spectroscopy and both techniques provide a full vibrational analysis of an entity being studied. Commercial Raman instruments typically utilize notch filters that block Rayleigh scattering and only allow for good quality Raman spectra to be obtained down to ~100 $cm^{-1}$. The spectral region from approximately 500 to 50 $cm^{-1}$ or lower, depending upon the type of filter, is referred to as the low frequency Raman spectral region. In this region, vibrational modes originate from the crystalline lattice of organic compounds, or from heavy atoms such as those incorporated into organometallic or inorganic molecules. The natural frequency of the crystal lattice is termed a phonon mode. Phonon modes arise from a fundamental structure, namely the specific crystal lattice for the particular compound being studied. Different crystalline forms typically display a unique crystal lattice, and therefore a unique phonon mode is displayed for each distinct crystalline form.

Low frequency (LF) Raman spectra became available owing to new filter designs, and it has been demonstrated that this region permits the identification/differentiation of different crystalline forms (See Roy, S., Chamberlin, B., and Matzger, A. J., "Polymorph Discrimination Using Low Wavenumber Raman Spectroscopy," Org. Process Res. Dev. 2013, 17, 976-980) The LF Raman spectroscopy allows the spectral acquisition in the Raman spectrum region, including Stokes region from 2200 $cm^{-1}$ to 0 $cm^{-1}$ and Anti-Stokes region from 0 $cm^{-1}$ to −900 $cm^{-1}$. The LF Raman spectroscopy allows observation of phonon modes (natural vibration frequency of the crystal lattice) which can be used to differentiate crystalline forms. The same "mirror image" signals corresponding to the phonon modes are visible in both Stokes and anti-Stokes regions, however, Stokes signals are normally used for differentiating crystalline forms owing to their stronger intensity than anti-Stokes signals.

LF Raman spectra were obtained using a Renishaw Raman, equipped with a ONDAX THz Raman system (excitation laser 853 nm, notch filter). The solid sample was analyzed with exposure time of 10 seconds and 32 accumulations. The solid sample was spread on a gold slide and analyzed using ONDAX TR-probe (Marqme TriX) contacting the solid sample. The LF-Raman was calibrated using sulfur reference standard prior to the sample analysis.

$^{13}C$ Nuclear Magnetic Resonance (NMR) Spectroscopy

The solid-state $^{13}C$ cross polarization magic angle spinning (CPMAS) experiments were carried out on a Bruker Avance II 400 spectrometer. Each sample (approximately 200 mg) was packed into a 4-mm zirconia rotor closed with Kel-F end caps for subsequent data acquisition. Adamantane, set to 29.5 ppm, was used as an external standard. Acquisition and processing parameters used are shown in the table below.

| Nucleus | $^{13}C$ |
|---|---|
| Temperature (K) | 297 |
| Observe Frequency (MHz) | 100.64 |
| Sweep Width (Hz) | 29762 |
| Dwell Time (μsec) | 16.8 |
| Acquisition Time (msec) | 275 |
| Recycle Delay (sec) | 20 |
| Spin Speed (kHz) | 7.0 |
| Number of Scans | 10240 |
| Processing Parameters | |
| Reference | external |
| Line Broadening (Hz) | 10 |

Example 1

Synthesis of (isobutyryloxy)methyl (1aR,7bS)-5-fluoro-2-hydroxy-1,1a,2,7b-tetrahydrobenzo[e]cyclopropa[c][1,2]oxaborinine-4-carboxylate (II')

Chloromethyl isobutyrate (8.9 mL, 70.4 mmol) was added to a heterogeneous mixture of compound (I) (5.0 g, 17.6 mmol), sodium bicarbonate (5.92 g, 70.4 mmol) and sodium iodide (1.62 g, 8.8 mmol) in acetonitrile (ACN) (25 mL) at room temperature. The heterogeneous mixture was heated at 55° C. After stirring at 55° C. for 16 hours, HPLC shows 93.6% conversion. The reaction mixture was cooled to 0° C. Ice-water (50 mL) was added and after stirring at 0° C. for 1 min MTBE (50 mL) was added. The layers were separated. The organic layer was washed several times with 20 mM $NaHCO_3$ (3×50 mL) and filtered through a 0.7 μm GMF syringe filter. The filtrate was concentrated to a few mL. ACN (25 mL) was added and the solution was concentrated to almost dryness at 25° C. The residual oil was taken in ACN (25 mL) and cooled to −5° C. Water (25 mL) was added and the turbid solution was cooled to −6° C. 2 N NaOH (7.1 mL) was added slowly until pH 9 keeping the temperature <−5° C. to obtain a biphasic mixture. The layers were separated (keep aqueous layer). The aqueous layer was extracted with heptane (25 mL, keep aqueous layer). The colorless aqueous layer was saturated with solid NaCl at room temperature to get a biphasic mixture. The layers were separated. The aqueous layer was back extracted with ACN (25 mL). The combined organic layers were concentrated to a few mL. ACN (25 mL) was added and the heterogeneous mixture was concentrated to a few mL. Isopropyl acetate (25 mL) was added and the heterogeneous solution was filtered through a 0.45 μm PTFE syringe filter to remove the residual salts. The clear filtrate was concentrated to dryness to get a colorless oily gel which was crystallized as described herein to give the sodium salt of compound (II) (i.e., compound (II')).

Example 2

Alternative Synthesis of (isobutyryloxy)methyl (1aR,7bS)-5-fluoro-2-hydroxy-1,1a,2,7b-tetrahydrobenzo[e]cyclopropa[c][1,2]oxaborinine-4-carboxylate (II')

Chloromethyl isobutyrate (5.6 mL, 44 mmol, 2.5 eq) was added to a heterogeneous mixture of compound (I) (5 g, 17.6 mmol), NaI (1.32 g, 8.8 mol, 0.5 eq) and crushed anhydrous $Na_2B_4O_7$ (5.31 g, 26.4 mmol, 1.5 eq) in anhydrous acetonitrile (25 mL) at room temperature. The reaction mixture was heated at 60° C. After stirring at 60° C. for 16 h and at room temperature for 2 days conversion was 97.5% by HPLC. The reaction mixture was cooled to room temperature, diluted with methyl tert-butyl ether (MTBE) (25 mL) and cooled to 0° C. Ice water (25 mL) was added at 0° C. After stirring 5 min at 0° C., the biphasic heterogeneous mixture was filtered over celite and the salts and pad were rinsed with MTBE. The clear biphasic filtrate was partitioned and organic layer was washed with water containing 20% brine (2×25 mL) then brine (25 mL). The organic layer was concentrated to dryness. The residual oil was taken up in ACN (25 mL) and cooled to 0° C. Cold water (15 mL) was added and the mixture was cooled to 0° C. 2 M Na$_2$CO$_3$ was added keeping temperature <5° C. (pH=7.6). 2 N NaOH then was added until pH 10.5 (7.6 mL). The slightly heterogeneous mixture was extracted with heptane (2×25 mL). The aqueous layer was saturated with solid NaCl and the layers were separated. The aqueous layer was back extracted with ACN (25 mL). The combined organic extracts were concentrated to dryness. The residual oil was taken up in ACN (25 mL) and concentrated to almost dryness. The residual oil was taken up isopropyl acetate (iPAc) (25 mL) and polish filtered through a 0.45 um syringe filter. The filtrate was concentrated to dryness. The residual oil was taken up in iPAc (3 mL), IPA (1 mL) and heptane (25 mL) to get a clear solution. Seeds were added followed by more heptane (25 mL). After stirring at room temperature for 30 minutes, a white slurry was obtained. After stirring at room temperature overnight, the solids were collected by filtration, rinsed with 17/3 heptane/IPAc (20 mL), air dried then dried under high vacuum to get compound (II') as a white powder 4.601 g, 72.2% yield, 99.67% purity, mp=145.4° C., form B.

resulted in significantly lower formation of the impurity isobutyryloxymethyl isobutyrate (IBOIB). The data is provided in the table below.

| Base (molar eq.) | Temp (° C.) | Chlromethyl isobutylrate eq | Time (h) | Conversion | IBOIB mol % |
|---|---|---|---|---|---|
| NaHCO$_3$ (4) | 55 | 4 | 15 | 90-95% | 80-100 |
| NaH$_2$PO$_4$ (1.5) | 65 | 3 | 16 | 97.3% | 15 |
| Na$_2$B$_4$O$_7$ (1.5) | 60 | 2.5 | 16 | 97-98% | 3-6 |
| Na$_2$B$_4$O$_7$ (1) | 60 | 2.5 | 16 | 97% | 10 |
| Na$_2$B$_4$O$_7$ (0.5) | 60 | 2.5 | 16 | 96% | 14 |
| Na$_2$B$_4$O$_7$ (1.5) | 70 | 2.5 | 8 | 98% | 4.7 |
| Na$_2$B$_4$O$_7$ (1.5) | 80 | 2.5 | 6 | 98.5% | 13 |

Example 4

Serum activation: Compounds 1, 2, or II were solubilized in water and added to rat, dog, monkey, and human serum at a concentration of 50 μg/mL. The samples were incubated at room temperature for 1 hour then assayed for "active" drug content using an LC/MS/MS assay. Microsomal activation: Compounds 1, 2, or II were solubilized in water and added to rat, dog, monkey, and human liver microsomes at a concentration of 1 μM. The samples were incubated at room temperature for 1 hour then assayed for "active" drug content using an LC/MS/MS assay.

TABLE 1

Prodrug activation data

| | 1 | 2 | II |
|---|---|---|---|
| Half-life human serum | >> 1 hour | >> 1 hour | >> 1 hour |
| Half-life rat serum | >> 1 hour | >> 1 hour | >> 1 hour |
| Half-life dog serum | >> 1 hour | >> 1 hour | >> 1 hour |
| Half-life monkey serum | >> 1 hour | >> 1 hour | >> 1 hour |
| Half-life human microsomes | 28 ± 2 min | 8 ± 1 min | 9 ± 5 min |
| Half-life rat microsomes | 3 ± 1 min | 3 ± 2 min | 5 ± 3 min |
| Half-life dog microsomes | 11 ± 1 min | 15 ± 1 min | 23 ± 2 min |
| Half-life monkey micorsomes | 2 ± 1 min | 3 ± 2 min | 2 ± 1 min |

Example 3

Effect of Base on Formation of Compound (II')

The effect of base was studied when preparing compound (II') according to the methods of Example 1 and 2 Changing the base from NaHCO$_3$ to NaH$_2$PO$_4$ resulted in an improved conversion of compound (I). Additionally, use of Na$_2$B$_4$O$_7$ resulted in a 96% conversion even with only 0.5 equivalents of base. Changing the base to either NaH$_2$PO$_4$ or Na$_2$B$_4$O$_7$ Example 5

Animals (rats, dogs, or monkeys) were administered compounds 1, 2, or II formulated in water by oral gavage. Blood samples were collected at various timepoints in EDTA containing tubes. After centrifugation, plasma samples were analyzed by LC/MS/MS for compounds 1, 2, or II as well as for "active" drug content. Bioavailability was determined by comparing the clearance after an intravenous dose of the "active" drug and the clearance of "active" drug after an oral dose of compounds 1, 2, or II.

TABLE 2

Pharmacokinetic data

|  | 1 | 2 | II |
|---|---|---|---|
| Oral bioavailability, rat (30 mg/kg) | 100% | 100% | 100% |
| Oral bioavailability, rat (100 mg/kg) | 100% | 46% | 100% |
| Oral bioavailability, dog (10 mg/kg) | 54% | 49% | 64% |
| Oral bioavailability, monkey (20 mg/kg) | 100% | 100% | 100% |
| Human microsome activation $t_{1/2}$ | 28 ± 2 min | 8 ± 1 min | 9 + 5 min |
| Crystallinity | Yes | No | Yes |
| Permeability/transport | High | High | High |

The oral bioavailability of Compound 2 at 100 mg/kg was 46%, while that of Compound 1 and Compound II were both 100%. Moreover Compound 2 is not crystalline, which may affect its stability. Compound 1 has significantly slower human microsomal activation than either Compound 2 or Compound II. Compound II has the best overall profile of a micosomally activated prodrug.

Example 6

Preparation of Crystal Form a of Compound (II')

At room temperature compound (II') is dissolved in a mixture of isopropyl acetate and isopropanol (volume ratio 1:0.2 or 2 mL isopropyl acetate per gram compound (II') and 0.4 mL isopropanol per g compound (II')). After complete dissolution, n-heptane (10 mL per g compound (II')) is rapidly added over a period of no longer than 1 hour. After addition of the n-heptane is complete the resulting slurry is stirred for a further 8 to 12 hours. The slurry is filtered and the filter cake is washed with a mixture of n-heptane and isopropyl acetate (volume ratio 9:1, 2 mL per g compound (II')) and dried.

Example 7

Alternative Preparation of Crystal Form a of Compound (II')

Compound II' was taken up in isopropyl acetate (5 mL) and the solution was heated at 50° C. Heptane (10 mL) was added followed by seeds (about 10 mg) and the mixture was stirred at 50° C. Over 30 min the mixture went from a clear solution with seeds stirring around to turbid to slightly heterogeneous to a thick slurry. Heptane (10 mL) was added for better stirring. After stirring at 50° C. for 2 h, heptane (10 mL) was added for better stirring and the slurry was cooled to room temperature. After stirring at room temperature for 2 h, heptane (10 mL) was added for better stirring. After stirring at rt over the weekend, the solids were collected by filtration, rinsed with κ/1 heptane/isopropyl acetate (2×10 mL), air dried then dried under high vacuum to give a white powder 4.24 g, 66.6% yield.

Example 8

Alternative Preparation of Crystal Form a of Compound (II')

Compound II' was taken up in hexanes and heated to 60-65° C. Ethyl acetate was added such that the ratio of hexanes:ethyl acetate was 85/15 (v/v). The mixture was cooled to 50° C. and stirred for 1 day at 50° C. The mixture was slowly cooled to room temperature and allowed to stand for three days at room temperature to give crystalline Form A of Compound II'

Example 9

Preparation Crystal Form B of Compound (II')

At room temperature, compound (II') is dissolved in a mixture of isopropyl acetate and isopropanol (volume ratio 1:0.2 or 2 mL isopropyl acetate per gram compound (II') and 0.4 mL isopropanol per g compound (II')). After complete dissolution, n-heptane (10 mL per g compound (II')) is slowly added over a period of at least 8 hours up to 12 hours. After addition of the n-heptane is complete the resulting slurry is stirred for a further 8 to 12 hours. The slurry is filtered and the filter cake is washed with a mixture of n-heptane and isopropyl acetate (volume ratio 9:1, 2 mL per g compound (II')) and dried.

Example 10

Alternative Preparation Crystal Form B of Compound (II')

At room temperature compound (II') is dissolved in a mixture of isopropyl acetate and isopropanol (volume ratio 1:0.2 or 2 mL isopropyl acetate per gram compound (II') and 0.4 mL isopropanol per g compound (II')). After complete dissolution, n-heptane (4 mL per g compound (II')) is added. The solution remains clear. Seed crystals of compound (II') Form B are added (10 mg per g compound (II')). Thereafter n-heptane (5 mL per g compound (II')) is slowly added over a period of at least 7 hours. After addition of the n-heptane is complete the resulting slurry is stirred for a further 8 to 12 hours. The slurry is filtered and the filter cake is washed with a mixture of n-heptane and isopropyl acetate (volume ratio 9:1, 2 mL per g compound (II')) and dried.

Example 11

Alternative Preparation Crystal Form B of Compound (II')

Compound II' (5 g scale) was taken up in isopropyl acetate (2.5 mL) and isopropanol (2.5 mL). Heptane (15 mL) was added followed by seeds (about 10 mg) and the mixture was stirred at room temperature. Over 30 min the mixture went from a clear solution with seeds stirring around to turbid to slightly heterogeneous to a thick slurry. Heptane (3×5 mL) was added over 1 h for better stirring. After stirring at room temperature for 16 h, the solids were collected by filtration, rinsed with 10/1/1 heptane/isopropyl acetate/isopropanol (2×10 mL), air dried then dried under high vacuum to give a white powder 4.24 g, 56.6% yield.

Example 12

Alternative Preparation Crystal Form B of Compound (II')

Compound II' (200 mg scale) was taken up in isopropanol (0.3 mL) and heated to 50° C. to form a mostly clear solution. After 5-10 additional minutes of heating at 50° C., solids began to precipitate. The solution was slowly cooled to room temperature, and the slurry was allowed to stand at room temperature for one day. The solids were collected, suspended in hexanes and isolated via vacuum filtration to give crystalline Form B of Compound II'.

What is claimed is:

1. A crystalline form of Compound II':

(II')

or a solvate thereof, wherein the crystalline form exhibits an X-ray powder diffraction pattern comprising at least three characteristic peaks, wherein said characteristic peaks are selected from approximately 4.3, 7.0, 7.2, 8.3, 11.0, 12.5, 15.0, 16.7, 17.5, 18.2, 19.1, 20.3, 22.3, 22.7, and 25.6 degrees 2θ.

2. The crystalline form of claim 1, wherein the crystalline form has an endotherm at about 141° C.

3. A compound having the structure of or a pharmaceutically acceptable salt of any of the foregoing.

4. The compound of claim 3, wherein the compound is anhydrous or a pharmaceutically acceptable salt thereof.

5. The compound of claim 3, wherein the pharmaceutically acceptable salt is the sodium salt.

6. A pharmaceutical composition comprising a therapeutically effective amount of a compound of claim 3, and a pharmaceutically acceptable excipient.

7. The pharmaceutical composition of claim 6, further comprising an additional medicament.

8. The pharmaceutical composition of claim 7, wherein the additional medicament is selected from the group consisting of an antibacterial agent, an antifungal agent, an antiviral agent, an anti-inflammatory agent, and an anti-allergic agent.

9. The pharmaceutical composition of claim 8, wherein the additional medicament is a β-lactam antibacterial agent.

10. The pharmaceutical composition of claim 9, wherein the β-lactam antibacterial agent is selected from the group consisting of Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefdericol, Cefditoren, Cefetamet, Cefmenoxime, Cefodizime, Cefoperazone, Cefotaxime, Cefpimizole, Cefpiramide, Cefpodoxime, Cefpodoxime protexil, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftolozane (CXA-101), RWJ-54428, MC-04,546, ME1036, Ceftiofur, Cefquinome, Cefovecin, RWJ-442831, RWJ-333441, and RWJ-333442.

11. The pharmaceutical composition of claim 9, wherein the β-lactam antibacterial agent is selected from the group consisting of Ceftazidime, Biapenem, Doripenem, Ertapenem, Imipenem, Meropenem, Tebipenem, Tebipenem pivoxil, Apapenem, and Panipenem.

12. The pharmaceutical composition of claim 9, wherein the β-lactam antibacterial agent is selected from the group consisting of Aztreonam, Tigemonam, BAL30072, SYN 2416, and Carumonam.

13. The pharmaceutical composition of claim 9, wherein the β-lactam antibacterial agent is tebipenem pivoxil.

14. The pharmaceutical composition of claim 9, wherein the β-lactam antibacterial agent is ceftibuten.

15. A method of treating a bacterial infection, comprising administering a compound according to claim 3 to a subject in need thereof.

16. The method of claim 15, further comprising administering to the subject an additional medicament.

17. The method of claim 16, wherein the additional medicament is an antibacterial agent, an antifungal agent, an antiviral agent, an anti-inflammatory agent, or an antiallergic agent.

18. The method of claim 17, wherein the additional medicament is a β-lactam antibacterial agent.

19. The method of claim 18, wherein the β-lactam antibacterial agent is selected from the group consisting of Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefdericol, Cefditoren, Cefetamet, Cefmenoxime, Cefodizime, Cefoperazone, Cefotaxime, Cefpimizole, Cefpiramide, Cefpodoxime, Cefpodoxime protexil, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftolozane (CXA-101), RWJ-54428, MC-04,546, ME1036, Ceftiofur, Cefquinome, Cefovecin, RWJ-442831, RWJ-333441, and RWJ-333442.

20. The method of claim 18, wherein the β-lactam antibacterial agent is selected from the group consisting of Ceftazidime, Biapenem, Doripenem, Ertapenem, Imipenem, Meropenem, Tebipenem, Tebipenem pivoxil, Apapenem, and Panipenem.

21. The method of claim 18, wherein the β-lactam antibacterial agent is selected from the group consisting of Aztreonam, Tigemonam, BAL30072, SYN 2416, and Carumonam.

22. The method of claim 18, wherein the β-lactam antibacterial agent is tebipenem pivoxil.

23. The method of claim 18, wherein the β-lactam antibacterial agent is ceftibuten.

24. The method of claim 15, wherein the infection comprises a bacteria selected from the group consisting of *Pseudomonas acidovorans, Pseudomonas alcaligenes, Pseudomonas putida, Burkholderia cepacia, Aeromonas hydrophilia, Francisella tularensis, Morganella morganii, Proteus mirabilis, Proteus vulgaris, Providencia alcalifaciens, Providencia rettgeri, Providencia stuartii, Acinetobacter baumannii, Bordetella pertussis, Bordetella para pertussis, Bordetella bronchiseptica, Haemophilus ducreyi, Pasteurella multocida, Pasteurella haemolytica, Branhamella catarrhalis, Borrelia burgdorferi, Kingella, Gardnerella vaginalis, Bacteroides distasonis, Bacteroides* 3452A homology group, *Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus*; or
wherein the infection comprises a bacteria selected from the group consisting of *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* and *Bacteroides splanchnicus.*

25. A method of preparing crystalline Form A or B of Compound II'

(II')

wherein crystalline Form A exhibits an X-ray powder diffraction pattern comprising at least three characteristic peaks, wherein said characteristic peaks are selected from approximately 4.3, 7.0, 7.2, 8.3, 11.0, 12.5, 15.0, 16.7, 17.5, 18.2, 19.1, 20.3, 22.3, 22.7, and 25.6 degrees 2θ;

wherein crystalline Form B exhibits an X-ray powder diffraction pattern comprising at least three characteristic peaks, wherein said characteristic peaks are selected from approximately 5.1, 7.0, 9.9, 11.0, 11.1, 14.1, 16.4, 17.1, 21.1, 22.3, 22.6, 26.9, and 28.3 degrees 2θ;

the method comprising the steps of:

(a) dissolving Compound II' in a solvent system to form a crystallization solution, wherein the solvent system consists of isopropyl acetate;

(b) heating the crystallization solution;

(c) adding heptane to the crystallization solution; and (d) adding seed crystals of crystalline Form A of Compound II' to the crystallization solution; or the method comprising the steps of:

(a) dissolving Compound II' in a solvent system to form a crystallization solution, wherein the solvent system consists of isopropyl acetate and isopropanol;

(b) adding heptane to the crystallization solution; and (c) adding seed crystals of crystalline Form B of Compound II' to the crystallization solution; or the method comprising the steps of:

(a) dissolving Compound II' in a solvent system to form a crystallization solution, wherein the solvent system consists of hexanes and ethyl acetate;

(b) heating the crystallization solution;

(c) initially cooling the crystallization solution;

(d) stirring the crystallization solution;

(e) further cooling the crystallization solution to room temperature; and (f) allowing the crystallization mixture to stand at room temperature; or the method comprising the steps of (a) dissolving Compound II' in isopropanol to form a crystallization solution;

(b) heating the crystallization solution; and cooling the crystallization solution to room temperature; or the method comprising the steps of (c) dissolving Compound II' in isopropanol to form a crystallization solution;

(d) heating the crystallization solution; and (e) cooling the crystallization solution to room temperature.

26. A method of preparing Compound II'

(II')

comprising the steps of:

combining Compound I (I)

or a salt thereof, a halomethyl isobutyrate, and a base in a polar organic solvent to form a reaction mixture 1; wherein the base is an inorganic base containing sodium; and heating the reaction mixture to a temperature of from about 50° C. to about 80° C. for a period of 0.5 to 24 hours.

27. A crystalline form of Compound II':

(II')

or a solvate thereof, wherein the crystalline form exhibits an X-ray powder diffraction pattern comprising at least three characteristic peaks, wherein said characteristic peaks are selected from approximately 5.1, 7.0, 9.9, 11.0, 11.1, 14.1, 16.4, 17.1, 21.1, 22.3, 22.6, 26.9, and 28.3 degrees 2θ.

28. The crystalline form of claim 27, wherein the crystalline form has an endotherm at about 152° C.

29. The crystalline form of claim 27, wherein the crystalline form is unsolvated.

30. The method of claim 26, wherein the base is $NaH_2PO_4$ or $Na_2B_4O_7$.

* * * * *